US008957106B2

(12) United States Patent
Dwek et al.

(10) Patent No.: US 8,957,106 B2
(45) Date of Patent: Feb. 17, 2015

(54) IMINOSUGAR TREATMENT OF TUMORS

(75) Inventors: Raymond Dwek, Oxford (GB); Wanda Buzgariu, Bucharest (RO); Anca Hirtopeanu, Bucharest (RO); Robert Moriarty, Chicago, IL (US); Gabriela Negroiu, Bucharest (RO); Norica Nichita, Bucharest (RO); Livia Zdrentu, Bucharest (RO); Nicole Zitzmann, Oxford (GB)

(73) Assignee: The Chancellor, Masters and Scholars of the University of Oxford, Oxford (GB)

( * ) Notice: Subject to any disclaimer, the term of this patent is extended or adjusted under 35 U.S.C. 154(b) by 1428 days.

(21) Appl. No.: 12/081,661

(22) Filed: Apr. 18, 2008

(65) Prior Publication Data

US 2008/0280972 A1    Nov. 13, 2008

Related U.S. Application Data

(60) Provisional application No. 60/913,560, filed on Apr. 24, 2007.

(51) Int. Cl.
| | |
|---|---|
| *A01N 43/36* | (2006.01) |
| *A61K 31/40* | (2006.01) |
| *A01N 31/00* | (2006.01) |
| *A61K 31/045* | (2006.01) |
| *C12N 5/071* | (2010.01) |
| *A61K 31/7004* | (2006.01) |

(52) U.S. Cl.
CPC ............. *A61K 31/40* (2013.01); *A61K 31/7004* (2013.01)
USPC ........................... 514/425; 514/724; 435/366

(58) Field of Classification Search
USPC .................................. 514/425, 724; 435/366
See application file for complete search history.

(56) References Cited

U.S. PATENT DOCUMENTS

| | | | |
|---|---|---|---|
| 5,229,523 A | 7/1993 | Wong et al. | |
| 5,276,120 A | 1/1994 | Wong et al. | |
| 5,461,143 A | 10/1995 | Wong et al. | |
| 5,579,823 A | 12/1996 | Mikol et al. | |
| 5,596,005 A | 1/1997 | Wong et al. | |
| 6,232,450 B1 | 5/2001 | Wong | |
| 6,462,193 B1 | 10/2002 | Wong et al. | |
| 6,774,140 B1 | 8/2004 | Wong et al. | |
| 2004/0147591 A1 | 7/2004 | Kanie et al. | |
| 2007/0088164 A1 | 4/2007 | Moriarity et al. | |

FOREIGN PATENT DOCUMENTS

WO    WO 2005/070418 A1    8/2005

OTHER PUBLICATIONS

Goss et al. Cancer Research, 1994, vol. 54, pp. 1450-1457.*
NCI Factsheet. Targeted Cancer Therapies, published online Dec. 2005, pp. 1-3.*
Myc et al. Cancer Research, 1989, vol. 49, pp. 2879-2883.*
Al Daher et al., "Change in specificity of glycosidase inhibition by N-alkylation of amino sugars," Biochem. J., 1989, 258(2), 613-615.
Altan et al, "Defective Acidification in Human Breast Tumor Cells and Implications for Chemotherapy," J. Exp. Med., May 18, 1998, 187(10):1583-1598.
Asano et al., "Glycosidase inhibitors: update and perspectives on practical use," Glycobiology, 2003, 13(10), 93R-104R.
Asano et al., "Sugar-mimic glycosidase inhibitors: natural occurrence, biological activity and prospects for therapeutic application," Tetrahedron: Asymmetry 2000, 11, 1645-1680.
Baldwin et al., "Rules for Ring Closure," J. Chem. Soc. Chem. Commun., 1976, 18, 734-736.
Block et al., "Secretion of human hepatitis B virus is inhibited by the imino sugar N-butyldeoxynojirimycin," Proc. Natl. Acad. Sci. U. S. A. Mar. 1994, 91(6), 2235-2239.
Bols, M. "1-Aza sugars, Apparent Transition State Analogues of Equatorial Glycoside Formation/Cleavage," Acc. Chem. Res. 1998, 31, 1-8.
Boucheron et al., "Design and synthesis of iminosugar-based inhibitors of glucosylceramide synthase: the search for new therapeutic agents against Gaucher disease," Tetrahedron: Asymmetry, 2005, 16(10), 1747-1756.
Branza-Nichita et al., "Antiviral Effect of N-Butyldeoxynojirimycin against Bovine Viral Diarrhea Virus Correlates with Misfolding of E2 Envelope Proteins and Impairment of Their Association into E1-E1 Heterodimers," J Virol. 2001, 75(8), 3527-3536.
Branza-Nichita et al., "Mutations at Critical N-Glycosylation Sites Reduce Tyrosinase Activity by Altering Folding and Quality Control," J. Biol. Chem., Mar. 17, 2000, 275(11):8169-8175.
Butters et al., "Imino sugar inhibitors for treating the lysosomal glycosphingolipidoses," Glycobiology, 2005, 15(10), 43R-52R.
Cao et al., "Biochemistry with temozolomide, cisplatin, vinblastine, subcutaneous interleukin-2 and interferon-α in patients with metastatic melanoma," Melanoma Research, 2006, 16(1):59-64.
Cenci di Bello et al., "Structure-activity relationship of swainsonine," Biochem. J., 1989, 259(3), 855-861.
Chapman et al., "Glyco- and Peptidomimetics from Three-Component Joullie-Ugi Coupling Show Selective Antiviral Activity," J. Am. Chem. Soc. 2005, 127, 506-507.

(Continued)

Primary Examiner — Samira Jean-Louis
(74) Attorney, Agent, or Firm — Foley & Lardner LLP

(57) ABSTRACT

A proliferation of cells can be reduced by contacting the cells with a compound having formula (I)

(I)

Figure 8:
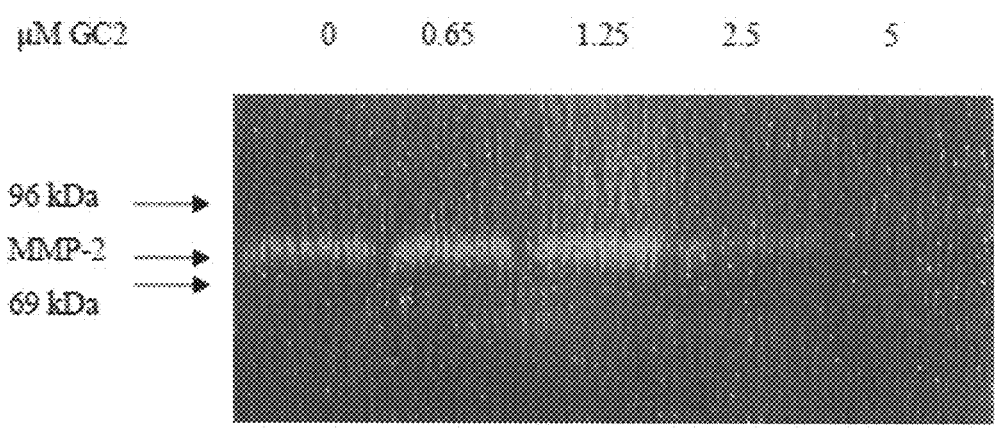

where R and R' are each alkyl groups, R" is hydrogen or an alkyl group and $X_3$, $X_4$ and $X_5$ are each independently selected from the group consisting of hydrogen, benzyl, t-butyldimethylsiloxy radical and triphenylmethyl. Accordingly, compounds of formula (I) can be used for treatment of tumors including melanoma. Also a secretion of a matrix metalloproteinase (MMP) enzyme by cells can be reduced by contacting the cells with the compound having formula (I). Accordingly, compounds of formula (I) can be used for treatment physiological conditions associated with an elevated MMP level, such as tumors.

35 Claims, 8 Drawing Sheets
(3 of 8 Drawing Sheet(s) Filed in Color)

(56) References Cited

OTHER PUBLICATIONS

Chapman et al., "Phase III Multicenter Randomized Trial of the Dartmouth Regimen Vresus Dacabazine in Patients with Metastatic Melanoma," J. Clinical Oncology, Sep. 1999, 17(9):2745-2751.
Chintala et al., "Induction of Matrix Metalloproteinase-9 Requires a Polymerized Actin Cytoskeleton in Human Malignant Glioma Cells," J. Biol. Chem., May 29, 1998, 273(22):13545-13551.
Cipolla et al., "Synthesis of Azasugars by Grignard Reaction on Glycosylamines," Tetrahedron, 1995, 51(16), 4679-4690.
Cook et al., "Species Dependent Esterase Activities for Hydrolysis of an Anti-HIV Prodrug Glycovir and Bioavailability of Active SC-48334," Pharmaceutical Research 1995, 12(8), 1158-1164.
Cuervo, Ana Maria, "Autophagy: in sickness and in health," Trends in Cell Biology, Feb. 2004, 14(2):70-77.
Daido et al., "Pivotal Role of the Cell Death Factor BNIP3 in Ceramide-Induced Autophagic Cell Death in Malignant Glioma Cells," Cancer Research, Jun. 15, 2004, 64:4286-4293.
Del Prete et al., "Combination Chemotherapy with Cisplatin, Carmustine, Dacarbazine and Tamoxifen in Metastatic Melanoma," Cancer Treatment Reports, Nov. 1984, 68(11):1403-1405.
Duff et al., "Synthesis of aza-C-disaccharides using cycloaddition reactions of a functionalized cyclic nitrone," Chem. Commun. 2000, 2127-2128.
Durantel et al., "Effects of Interferon, Ribavirin, and Iminosugar Derivatives on Cells Persistently Infected with noncytopathic Bovine Viral Diarrhea Virus," Antimicrob. Agents and Chemother., 2004, 48(2), 497-504.
Durantel et al., "Study of the Mechanism of Antiviral Action of Iminosugar Derivatives against Bovine Viral Diarrhea Virus," J Virol. 2001, 75(19), 8987-8998.
Evans et al., "Addition of Lithiated 9-Deazapurine Derivatives to a Carbohydrate Cyclic Imine: Convergent Synthesis of the Aza-C-nucleoside Immucillins," J. Org. Chem. 2001, 66, 5723-5730.
Evans et al., "Synthesis of Transition State Analogue Inhibitors for Purine Nucleoside Phosphorylase and N-Riboside Hydrolases," Tetrahedron 2000, 56, 3053-3062.
Fleet et al., "Practical synthesis of deoxymannojirimycin and mannonolactam from L-gulonolactone. Synthesis of L-deoxymannojirimycin and L-mannonolactam from D-gulonolactone," Tetrahedron 1989, 45(1), 319-326.
Fleet et al., "Short Efficient Synthesis of the $\alpha$-L-Fucosidase Inhibitor, Deoxyfuconojirimycin [1,5-Dideoxy-1,5-imino-L-fucitol} from D-Lyxonolactone," J. Chem. Soc. Perkin Trans 1, 1989, 665-666.
Fleet et al., "Short synthesis of D-deoxymannojirimycin and D-mannonolactam from L-gulonolactone and of L-deoxymannojirimycin and L-mannonolactam from D-gulonolactone," Tetrahedron Letters 1988, 29(23), 2871-2874.
Furneaux et al., "Synthesis of Transition State Inhibitors for N-Riboside Hydrolases and Transferases," Tetrahedron 1997, 53, 2915-2930.
Ganem, B., "Inhibitors of Carbohydrate-Processing Enzymes: Design and Synthesis of Sugar-Shaped Heterocycles," Acc. Chem. Res 1996, 29, 340-347.
Gijsbers et al., "GCP-2/CXCL6 synergizes with other endothelial cell-derived chemokines in neutrophil mobilization and is associated with angiogenesis in gastrointestinal tumors," Experimental Cell Research, 2005, 303:331-342.
Godseken et al., "Deoxyiminoalditols from Aldonolactones—V. Preparation of the Four Stereoisomers of 1,5-Dideoxy-1,5-iminopentitols. Evaluation of these Iminopentitols and Three 1,5-Dideoxy-1,5-iminoheptitols as Glycosidase Inhibitors," Bioorg. Med. Chem., 1996, 4(11), 1857-1865.
Gogskesen et al., "Unusual ring contraction by substitution of 4-O-activated-pentono-1,5-lactams with cyanide. Stereospecific synthesis of 6-amino-1,4,5,6-tetradeoxy-1,4-imino-hexitols," Tetrahedron: Asymmetry 2000, 11, 567-579.
Goodyear et al., "The Oxide-ring Structure of Normal and $\gamma$-Derivates of Mannose . . . " J. Chem. Soc. 1927, 3136-3146.
Gozuacik et al., "Autophagy as a cell death and tumor suppressor mechanism," Oncogene, 2004, 23:2891-2906.
Grossman et al., "Drug resistance in melanoma: Mechanisms, apoptosis, and new potential therapeutic targets," Cancer and Metastasis Reviews, 2001, 20:3-11.
Han et al., "Mannich-Type C-Nucleosidations with 7-Carba-purines and 4-Aminopyrimjidines," Synlett 2005, 5, 744-750.

Han et al., "Spectroscopic, Crystallographic and Computational Studies of the Formation and Isomerization of Cyclic Acetals and ketals of Pentonolactones," Tetrahedron: Asymmetry 1994, 5(12), 2535-2562.
Heightman et al., "Recent Insights into Inhibition, Structure, and Mechanism of Configuration-Retaining Glycosidases," Angew. Chem. Int. Ed. Engl. 1999, 38, 750-770.
Horenstein et al., "A New Class of C-Nucleoside Analogues. 1-(S)-aryl-1,4-dideoxy-1,4-imino-D-ribitols, Transition State Analogue Inhibitors of Nucleoside Hydrolase," Tetrahedron Lett. 1993, 34(45), 7213-7216.
Joseph et al., "Syntheses of (3R,4R,5R,6R)-tetrahydroxyazepane (1,6-dideoxy-1,6-imino-D-mannitol) and (3S, 4R, 5R, 6F)-tetrahydroxyazepane (1,6-dideoxy-1,6-imino-D-glucitol)," Tetrahedron 2002, 58, 6907-6911.
Kabeya et al., "LC3, a mammalian homologue of yeast Apg8p, is localized in autophagosome membranes after processing," The EMBO Journal, 2000, 19(21):5720-5728.
Kanzawa et al., "Induction of Autophagic Cell Death in Malignant Glioma Cells by Arsenic Trioxide," Cancer Research, May 1, 2003, 63:2103-2108.
Kanzawa et al., "Role of autophagy in temozolomide-induced cytotoxicity for malignant glioma cells," Cell Death and Differentiation, 2004, 11:448-457.
Karpas et al., "Aminosugar derivatives as potential anti-human immunodeficiency virus agents," PNAS US 1988, 85(23), 9229-9233.
Khayat et al., "Fotemustine in the Treatment of Brain Primary Tumors and Metastases," Cancer Investigation, 1994, 12(4):414-420.
Klionsky et al., "Autophagy as a Regulated Pathway of Cellular Degradation," Science, Dec. 1, 2000, 290:1717-1721.
Krishan et al., "Rapid flow cytofluorometric analysis of mammalian cell cycle by propidium iodide staining," J. Cell Biology, 1975, 66:188-193.
Legler, G. "Glycoside hydrolases: Mechanistic Information from studies with reversible and irreversible inhibitors," Adv. Carbohydr. Chem. Biochem. 1990, 48, 319-385.
Lev et al., "Exposure of Melanoma Cells to Dacarbazine Results in Enhanced Tumor Growth and Metastasis In Vivo," J. Clin. Oncology, Jun. 1, 2004, 22(11):2092-2100.
Levade et al., "Ceramide in Apoptosis: A Revisited Role," Neurochemical Research, Aug. 2002, 27(7/8):601-607.
Li et al., "Chemotherapy-induced apoptosis in melanoma cells is p53 dependent," Melanoma Research, 1998, 8:17-23.
Look et al., "Enzyme-Catalyzed Organic Synthesis: Practical Routes to Aza Sugars and Their Analogs for Use as Glycoprocessing Inhibitors," Acc. Chem. Res 1993, 26, 182-190.
Lu et al., "Aberrant trafficking of hepatitis B virus glycoproteins in cells in which N-glycan processing is inhibited," PNAS USA 1997, 94(6) 2380-2385.
Lu et al., "Evidence that N-linked glycosylation is necessary for hepatitis B virus secretion," Virology, 1995, 213(2), 660-665.
Lu et al., "The Alkylated Imino Sugar, n-(n-Nonyl)-Deoxygalactonojirimycin, Reduces the Amount of Hepatitis B Virus Nucleocapsid in Tissue Culture," J. Virol. 2003, 77(22), 11933-11940.
Lundt et al., "Deoxyiminoalditols from Aldonolactones. III. Preparation of 1,4-Dideoxy-1,4-imino-L-gulitol. —Evaluation of 1,4-Dideoxy-1,4-iminohexitols as Glycosidase Inhibitors," Tetrehedron, 1994, 50(25), 7513-7520.
Manna et al., "2,3,4-Tri-O-acetyl-1,6-anhydro-$\beta$-D-mannopyranose, an artifact produced during carbohydrate analysis. A total synthesis of 2,3,5-tri-O-acetyl-1,6-anhydro-$\beta$-D-mannofuranose," Carbohydr. Res. 1993, 243, 11-27.
Mehta et al., "Imino sugars that are less toxic but more potent as antivirals, in vitro, compared with N-n-nonyl DNJ," Antivir. Chem. Chemother. 2002, 13(5), 299-304.
Mehta et al., "Inhibition of Hepatitis B Virus DNA Replication by Imino sugars Without the Inhibition of the DNA Polymerase: Therapeutic Implications," Hepatology, 2001, 33(6), 1488-1495.
Mehta et al., "Structure-Activity Relationship of a New Class of Anti-Hepatitis B Virus Agents,"Antimicrob. Agents and Chemother. 2002, 46(12), 4004-4008.
Mehta et al., "$\alpha$-Galactosylceramide and Novel Synthetic Glycolipids Directly Induce the Innate Host Defense Pathway and Have Direct Activity against Hepatitis B and C Viruses," Antimicrob. Agents. Chemother., 2004, 48(6), 2085-2090.

(56) References Cited

OTHER PUBLICATIONS

Mellor et al., "Preparation, biochemical characterization and biological properties of radiolabelled Nalkylated deoxynojirimycins," Biochem. J., 2002, 366, 225-233.
Mizushima, Noboru, "Methods for monitoring autophagy," Intl. J. Biochem. & Cell Biology, 2004, 36:2491-2502.
Moriarty et al., "exo-Imino to endo-Iminocyclitol Rearrangement. A General Route to Five-membered Antiviral Azasugars," Org. Lett., 2006, 8(16) 3465-3467.
Morton et al., "Vaccine Therapy for Malignant Melanoma," CA Cancer J. Clin., 1996, 46:225-244.
Negroiu et al., "Folding and Maturation of Tyrosinase-related Protein-1 Are Regulated by the Posttranslational Formation of Disulfide Bonds and by N-Glycan Processing," J. Biol. Chem., Oct. 13, 2000, 275(40):32200-32207.
Negroiu et al., "Protein specific N-glycosylation of tyrosinase and tyrosinase-related protein-1 in B16 mouse melanoma cells," Biochem. J., 1999, 344:659-665.
Negroiu et al., "The Inhibition of Early N-Glycan Processing Targets TRP-2 to Degradation in B16 Melanoma Cells," J. Biol. Chem., Jul. 18, 2003, 278(29):27035-27042.
O Hagan, D., "Pyrrole, pyrrolidine, pyridine, piperidine, azepine and tropane alkaloids," Nat. Prod. Rep. 1997, 14, 637-651.
O'Reilly et al., "Temozolomide: A New Oral Cytotoxic Chemotherapeutic Agent with Promising Activity Against Primary Brain Tumours," Eur. J. Cancer, 1993, 29A(7):940-942.
Ogura et al., "Reaction of Ethynyl Compounds with Lactones," J. Org. Chem. 1972, 37, 72-75.
Paglin et al., "A Novel Response of Cancer Cells to Radiation Involves Autophagy and Formation of Acidic Vesicles," Cancer Research, Jan. 15, 2001, 61:439-444.
Pearson et al., "Recent Advances in the total Synthesis of Piperidine Azasugars," Eur. J. Org. Chem. 2005, 2159-2191.
Petrescu et al., "Tyrosinase and Glycoprotein Folding: Roles of Chaperones That Recognize Glycans," May 9, 2000, 39(18):5229-5237.
Richards et al., "Effective Chemotherapy for Melanoma After Treatment with Interleukin-2," Cancer, Jan. 15, 1992, 69(2):427-429.
Rubtsova et al., "Disruption of active microfilaments by cytochalasin D leads to activation of p53," FEBS Letters, 1998, 430:353-357.
Rucklidge et al., "Cell-adhesion molecules and metalloproteinases: a linked role in tumour cell invasiveness," Biochemical Society Transactions, 648th Meeting, Belfast, Feb. 1994, 22(1), 7 pages.
Saotome et al., "Combinatorial library of five-membered iminocyclitol and the inhibitory activities against glycol-enzymes," Chemistry & Biology, 2001, 8, 1061-1070.
Sawada et al., "Betulinic acid augments the inhibitory effects of vincristine on growth and lung metastasis of B16F10 melanoma cells in mice," British Journal of Cancer, 2004, 90:1672-1678.
Scarlatti et al., "Ceramide-mediated Macroautophagy Involves Inhibition of Protein Kinase B and Up-regulation of Beclin 1," J. Biol. Chem., Apr. 30, 2004, 279(18):18384-18391.
Sifferlen et al., "Chiral 5-Methyl-trihydroxypyrrolidines-Preparation from 1,2-Oxazines and Glycosidase Inhibitory Properties," Tetrahedron, 2000, 56, 971-978.
Sletten et al., "A Flexible Stereospecific Synthesis of Polyhydroxylated Pyrrolizidines from Commercially Available Pyranosides," J. Org. Chem., 2006, 71, 1335-1343.
Stover et al., "Systemic Delivery of Liposomal Short-Chain Ceramide Limits Solid Tumor Growth in Murine Models of Breast Adenocarcoma," Clin. Cancer Res., May 1, 2005, 11(9):3465-3474.
Stütz et al., "Iminosugars as Glycosidase Inhibitors, Nojirymycin and Beyond," 1999, Table of Contents, 8 pages.
Stütz, A. E., "8: Some Reflections on Structure-Activity Relationships in Glycosidase-Inhibiting Iminoalditols and Iminosugars," Iminosugars as Glycosidase Inhibitors: Nojirimycin and Beyond; Ed. Wiley-VCH: Weinheim, 1999, 157-187.
Stütz, A. E., "A Novel Approach for Clarifying the Reaction Mechanism of Retaining Glycoside Hydrolases," Angew. Chem. Int. Ed. Engl. 1996, 35, 1926-1928.
Tam et al., "Chiral Models of the Furenone Moiety of Germacranolid Sesquiterpenes," J. Org. Chem., 1980, 45, 1344-1346.
Tenud et al., "Endocyclishce $S_N$-Reaktionen am gesattigten Kohlenstoff?," Helv. Chim. Acta, 1970, 53(8), 2059-2069.
Ting et al., "Targeting a Novel *Plasmodium falciparum* Purine Recycling Pathway with Specific Immucillins," J. Biol. Chem. 2005, 280(10), 9547-9554.
Tuchscherer et al., "The Tasp Concept: Mimetics of peptide ligands, protein surfaces and folding units," Tetrahedron, 1993, 49(16), 3359-3575.
Van Engeland et al., "Annexin V-Affinity Assay: A Review on an Apoptosis Detection System Based on Phosphatidylserine Exposure," Cytometry, 1998, 31:1-9.
Vonlanthen et al., "Hydroxycyclopentanone Derivatives from D-Mannose via Ring Closing Metathesis: An Improved Synthesis of a Key Intermediate of Tricyclo-DNA," Synthesis 2003, 7, 1087-90.
Wang et al., "Chemo-enzymatic Synthesis of Five-membered Azasugars as Inhibitors of Fucosidase and Fucosyltransferase: An Issue Regarding the Stereochemistry Discrimination at Transition States," Tetrahedron Lett., 1993, 34(3), 403-406.
Wang et al., "Synthesis and Biological Evaluation of Glycosidase Inhibitors: *gem*-Difluoromethylenated Nojirimycin Analogues," J. Med. Chem., 2006, 49, 2989-2997.
Winchester et al., "Amino-sugar glycosidase inhibitors: versatile tools for glycobiologists," Glycobiology 1992, 2, 199-210.
Yamazaki et al., "Regulation of cancer cell motility through actin reorganization," Cancer Soc., Jul. 2005, 96(7):379-386.
Yao et al., "Molecular response of human glioblastoma multiforme cells to ionizing radiation: cell cycle arrest, modulation of the expression of cyclin-dependent kinase inhibitors, and autophagy," J. Neurosurg., 2003, 98:378-384.
Zhang et al., "Disruption of G1-phase phospholipid turnover by inhibition of $Ca^{2+}$—independent phospholipase $A_2$ induces a p53-dependent cell-cycle arrest in G1 phase," J. Cell Science, 2006, 119(6):1005-1015.
Ziegler-Heitbrock et al., "In Vitro Differentiation of Human Melanoma Cells Analyzed with Monoclonal Antibodies," Cancer Research, Mar. 1985, 45:1344-1350.
Zitzmann et al., "Imino sugars inhibit the formation and secretion of bovine viral diarrhea virus, a pestivirus model of hepatitis C virus: Implications for the development of broad spectrum anti-hepatitis virus agents," Proc. Natl. Acad. Sci. USA, 1999, 96(21), 11878-11882.
International Search Report and Written Opinion mailed Jun. 15, 2009 in corresponding PCT/US2008/060822, 19 pages.
Guerrera et al., "N-butyldeoxynojirimycin inhibits murine melanoma cell ganglioside metabolism and delays tumor onset," Medline, Jan. 1, 1900, XP003007567, 1 page. (abstract of Cancer Letters, Ireland, Nov. 10, 2003, vol. 201).
Martin, O., "Iminosugars: current and future therapeutic applications," Annales Pharmaceutiques Francaises, Jan. 2007, 65(1):5-13, with English abstract.
Cipolla et al., "General Methods for Iminosugar Synthesis," Current Topics in Medicinal Chemistry, 2003, 3:485-511.
Yang et al., "Stereochemistry in the Synthesis and Rection of exo-Glycals," J. Org. Chem., 2002, 67:3773-3782.

* cited by examiner

FIGURES 1(A)-(B)
A
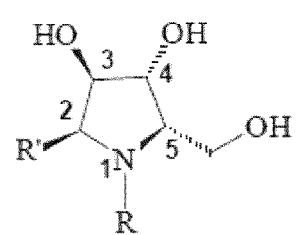
B
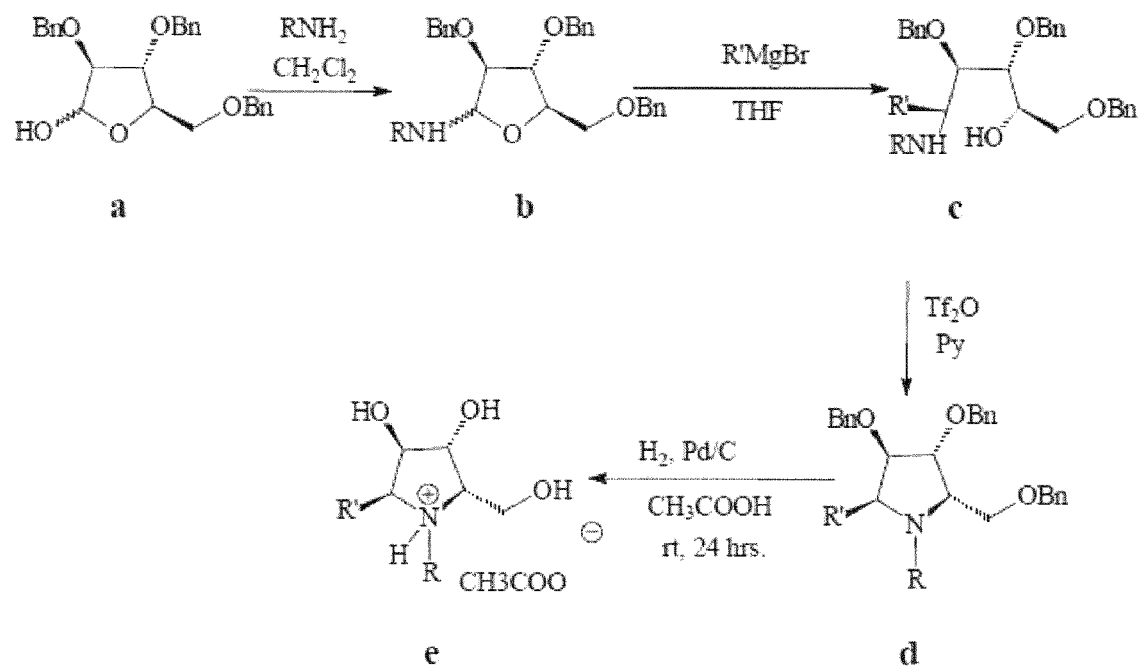

FIGURES 2(A)-(B)
A
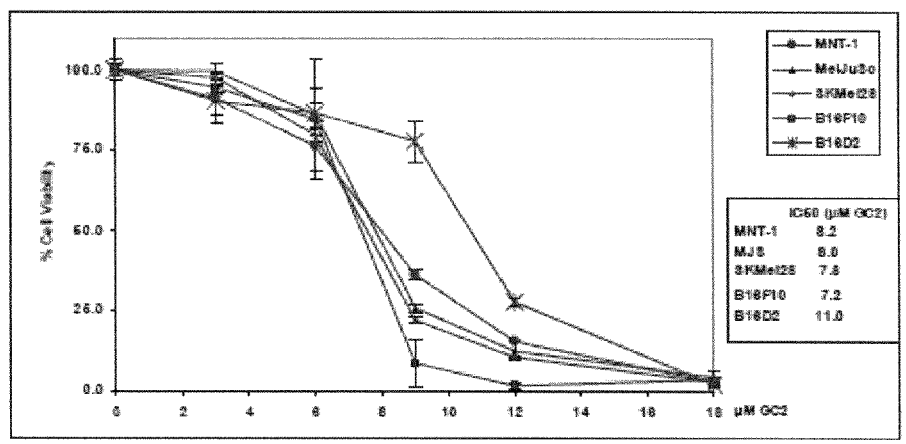
B
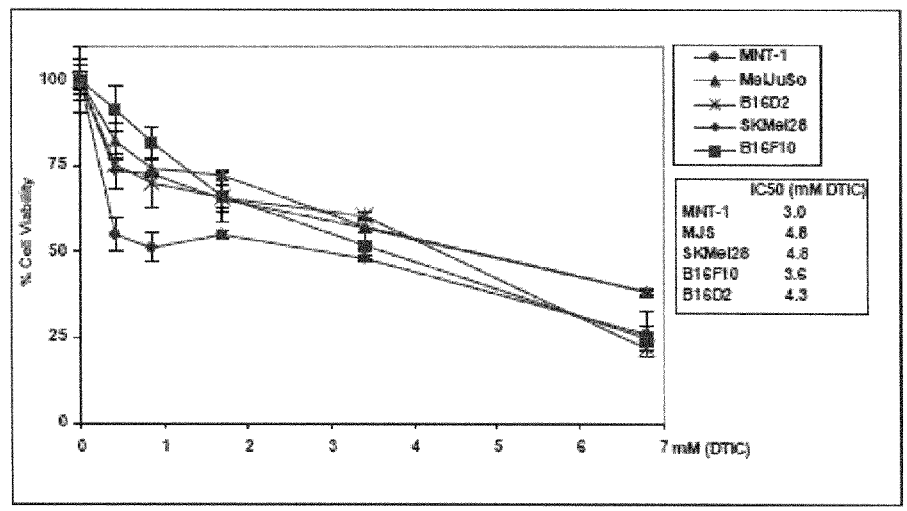

FIGURE 3(a)-(d)
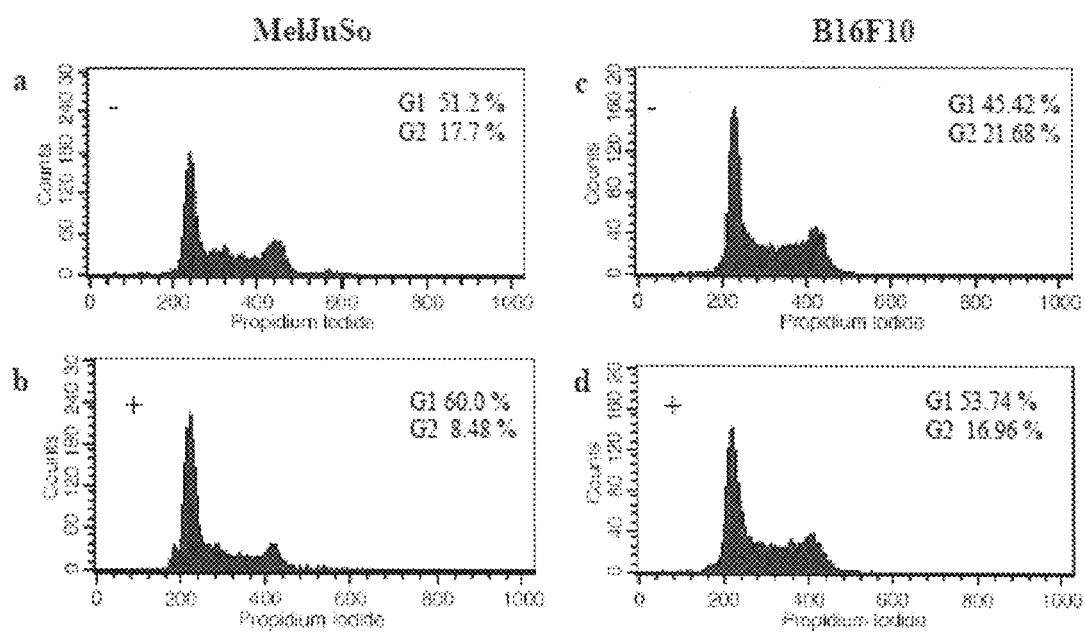

FIGURES 4(A)-(C)
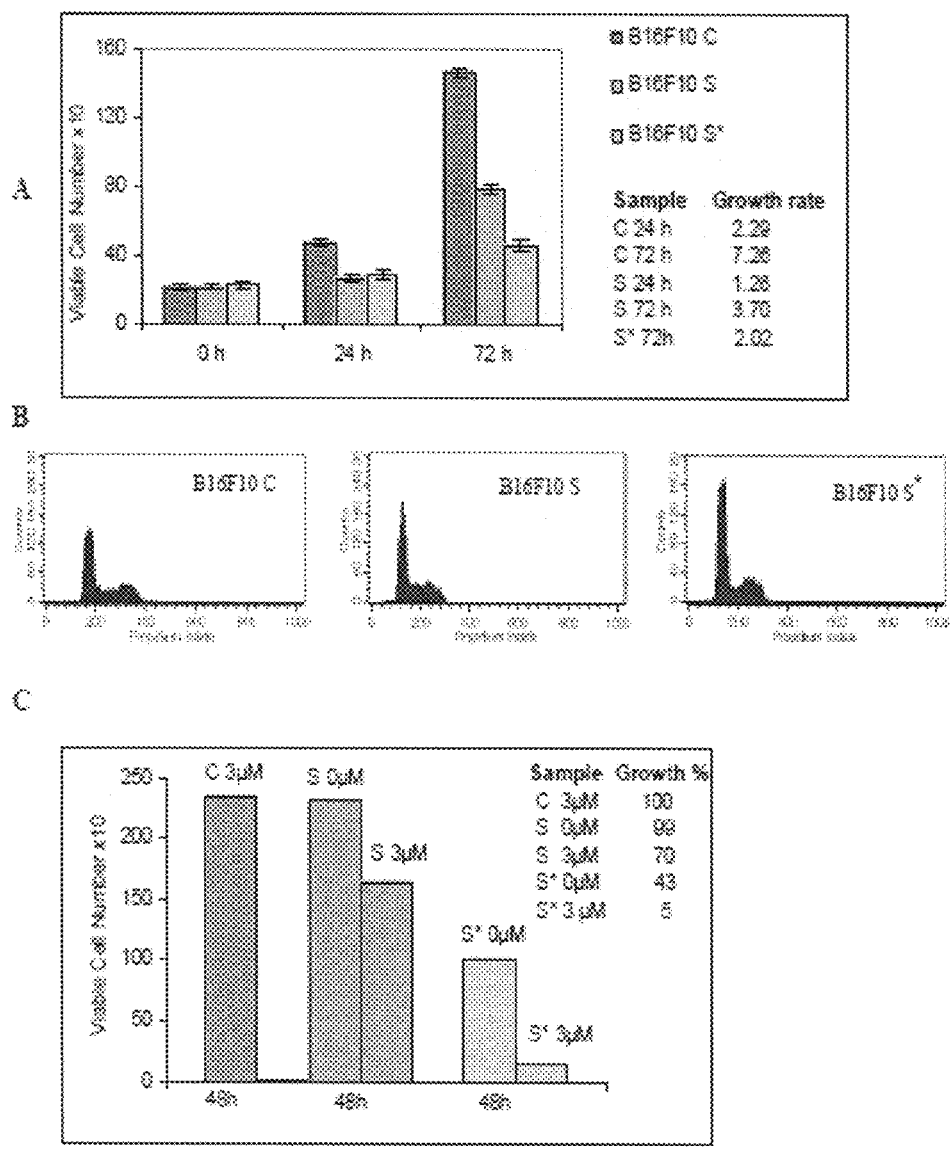

FIGURES 5(A)-(B)
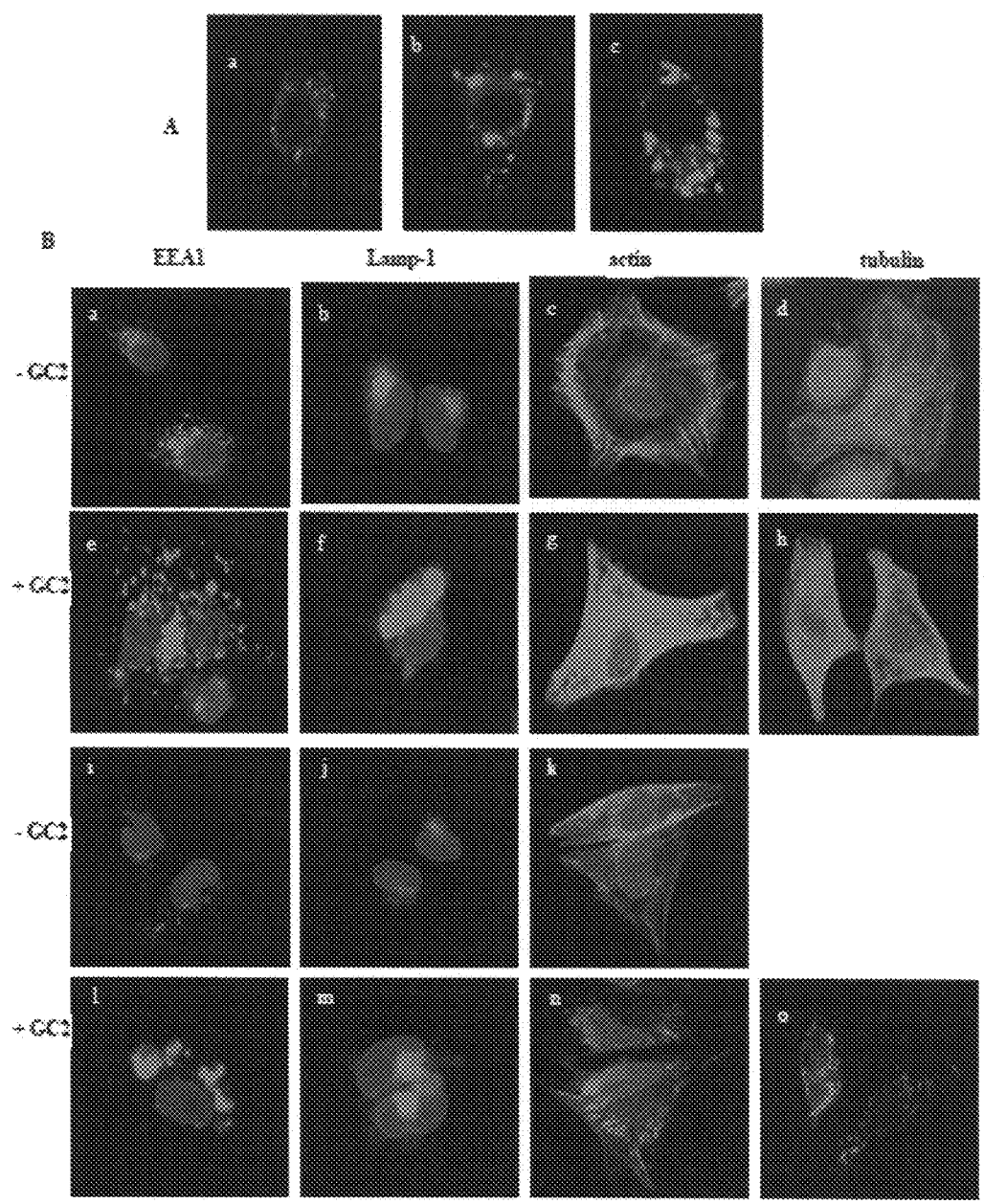

FIGURES 6(A)-(C)
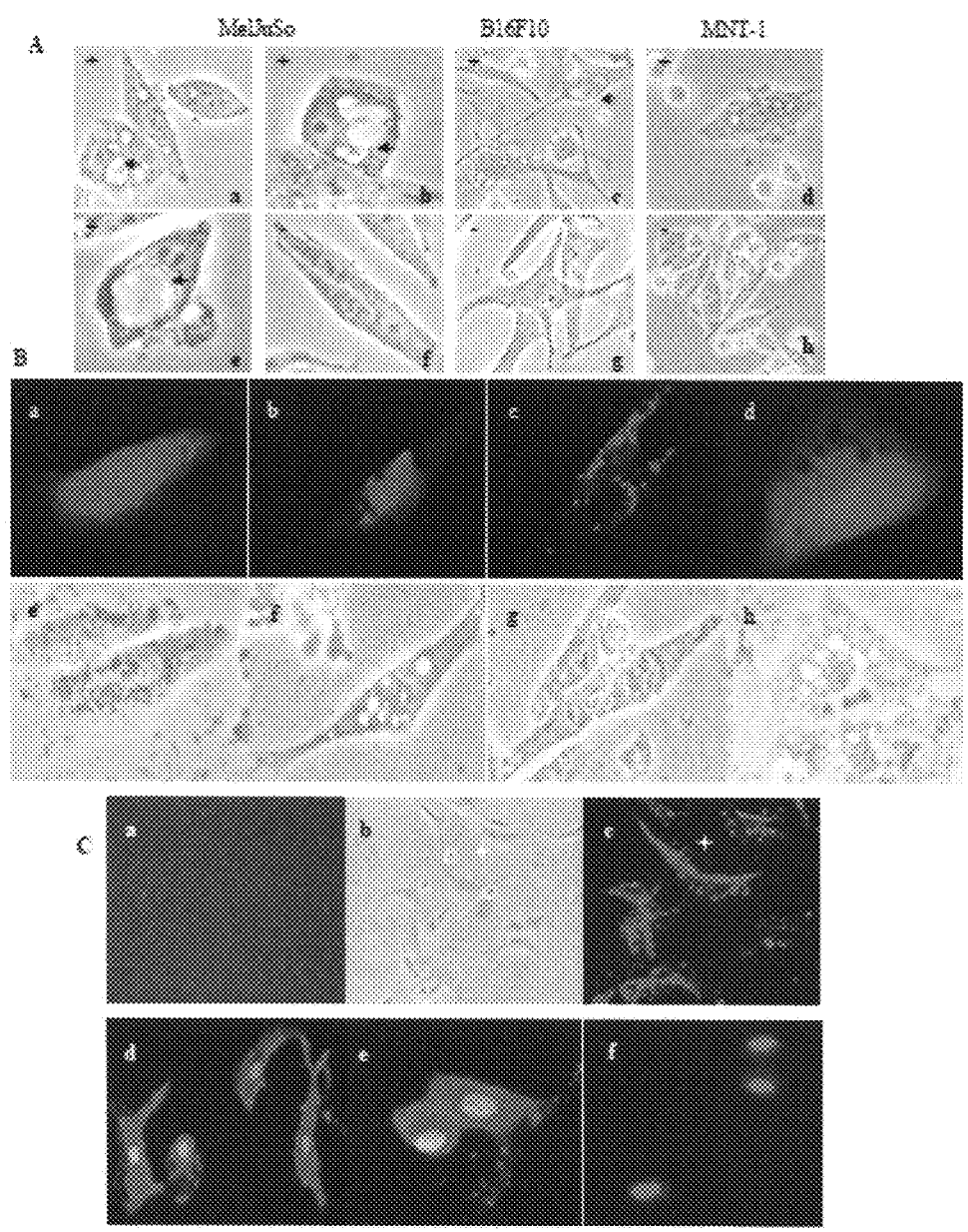

FIGURES 7(A)-(B)
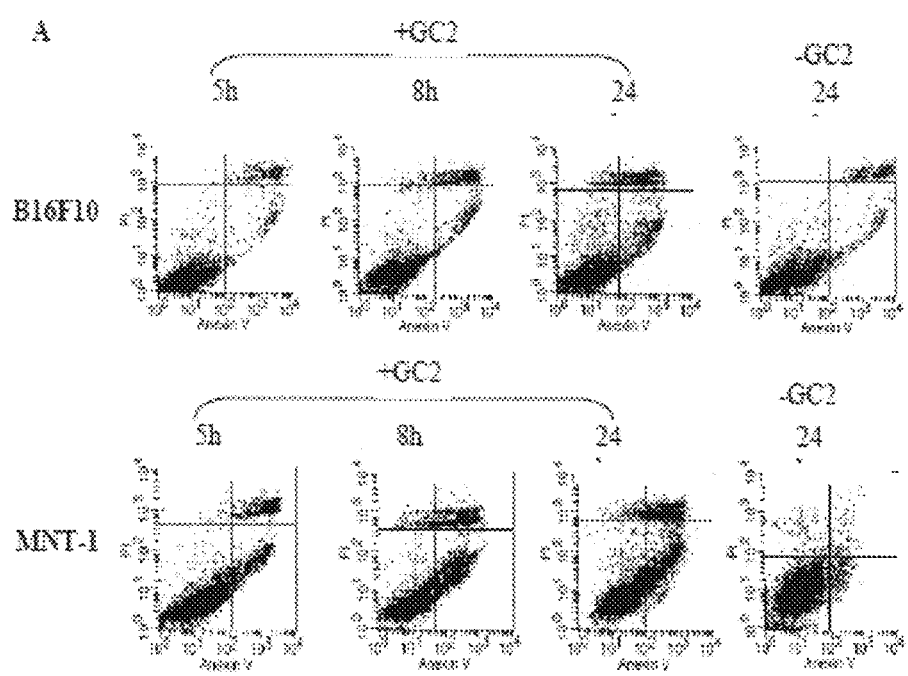

IMINOSUGAR TREATMENT OF TUMORS

CROSS-REFERENCE TO RELATED APPLICATIONS

This application claims priority from U.S. Provisional Application No. 60/913,560, filed Apr. 24, 2007, the entire contents of which are incorporated herein by reference.

BACKGROUND

The present application relates to treatment of tumors and, more particularly, to treatment of tumors with iminosugars.

Melanoma is a malignancy of pigment-producing cells (melanocytes) occurring in skin, eyes, ears, gastrointestinal tract, leptomeninges of the central nervous system and oral and genital mucous membranes. Although melanoma accounts for only 4% of all skin cancers, it causes the greatest number of skin cancer-related deaths worldwide. Despite numerous therapeutic strategies no standard therapy exists for patients with metastatic melanoma. The treatment options include monochemotherapy, see e.g. Chapman, P. B., et al. J. Clin. Oncol. 17, 2745-2751, 1999, O'Reilly, et al. Eur. J. Cancer 29A, 940-942, 1993, Khayat, D., et al. Cancer Invest., 12, 414-420, 1994; polychemotherapeutical approaches, see e.g. DelPrete, S. A., et. al. Cancer Treat. Rep. 12, 1343, 1983; immunomodulatory therapies, such as interferon-α and interleukin-2, see e.g. Richards, J. M., et al., Cancer, 69, 427-429, 1992; as well as vaccination therapy with dendritic cells or genetically modified tumor cells, see e.g. Morton, D. L., Barth, A. Ca. Cancer J. Clin. 46, 225-244, 1996, and biochemotherapy, see e.g. Gonzales Cao, M., et al., Melanoma Res. 16, 59-64, 2006.

Melanoma cells can be highly proliferative and invasive. The specific mechanisms conferring intrinsic and acquired drug resistance in melanoma cells are so far poorly understood and difficult to be controlled. Moreover, classical agents, such as dacarbazine, generally considered the most active agent for treating malignant melanoma and approved by the FDA, is not only ineffective, but can be hazardous and counterproductive, resulting in the selection of more chemoresistant cell lines with enhanced tumorogenic and metastatic potential, see e.g. Lev, D., et al., J. Clin. Oncol. 22, 2092-2100, 2004. Thus, a need exists to develop alternative methods for treatment of melanoma.

SUMMARY OF THE INVENTION

According to one embodiment, a method of reducing proliferation of cells comprises contacting the cells with a compound having formula I or a pharmaceutically acceptable salt thereof:

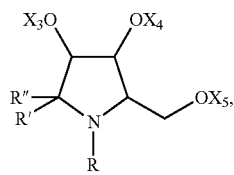

(I)

wherein R is an alkyl group comprising from 1 to 20 carbon atoms, R' is an alkyl group comprising from 1 to 20 carbon atoms, R" is hydrogen or an alkyl group comprising from 1 to 20 carbon atoms; and $X_3$, $X_4$ and $X_5$ are each independently selected from the group consisting of hydrogen, benzyl, t-butyldimethylsiloxy radical and triphenylmethyl, wherein the contacting results in a reduced proliferation of the cells.

According to another embodiment, a method of reducing a secretion of a matrix metalloproteinase enzyme in cells comprises contacting the cells with a compound having the formula I or a pharmaceutically acceptable salt thereof:

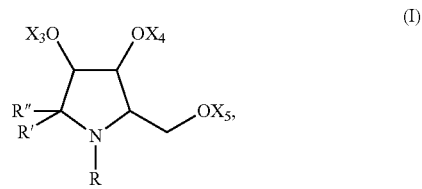

(I)

wherein R is an alkyl group comprising from 1 to 20 carbon atoms, R' is an alkyl group comprising from 1 to 20 carbon atoms, R" is hydrogen or an group alkyl comprising from 1 to 20 carbon atoms and $X_3$, $X_4$ and $X_5$ are each independently selected from the group consisting of hydrogen, benzyl, t-butyldimethylsiloxy radical and triphenylmethyl, wherein the contacting results in a reduced secretion of the matrix metalloproteinase enzyme in the cells.

DRAWINGS

This application contains at least one drawing executed in color. Copies of this patent application publication with color drawings will be provided by the Office upon request and payment of the necessary fee.

FIGS. 1 (A)-(B) illustrate GC2 chemistry. (A) shows a chemical structure of GC2; (B) presents synthesis and purification pathway of GC2 starting from 2,3,5-tri-O-benzyl-D-arabynofuranose.

FIGS. 2 (A) and (B) demonstrate an effect of GC2 and DTIC respectively on a viability of melanoma cells. Melanoma cell lines were exposed to increasing concentrations of GC2 (A) or DTIC (B) for 24 h, and cell viability was tested by MTS assay and expressed as % of untreated controls. Data shown present an average over three independent experiments. IC50 values representing GC2 or DTIC concentrations achieving 50% cell viability were calculated for each cell line.

FIGS. 3 (a)-(d) demonstrate cell cycle analysis of GC2-treated melanoma cells. MelJuSo (a and b) and B16F10 (c and d) cells were cultured for 24 h without (−) or with (+) 6 μM of GC2. Adherent cells were harvested, labeled with PI and analyzed for a cell cycle. In both cell lines, the G1 population increased in treated cells (b and d) compared to untreated controls (a and c).

FIGS. 4 (A)-(C) demonstrate an effect of drug scheduling on a viability of melanoma GC2 treated cells and their progenies. FIG. 4(A). Equal numbers of B16F10 cells were cultured for 24 h and 72 h, in the absence of GC2 (C), with a single GC2 dose of 6 μM (S) or with multiple 6 μM GC2 doses, each freshly added every 24 h (S*). Adherent cells were harvested and vital cells detected as Trypan Blue negative were counted. The growth rate of controls and samples was calculated as ratio between cell number after 24 h or 72 h and the initial cell number in sample C, or before the drug was added in samples S and S*. FIG. 4(B). Cells from samples C, S and S* after 72 h of incubation were analyzed for a cell cycle. FIG. 4(C). Equal number of cells previously cultured for 72 h as explained in FIG. 4(A), were further incubated for 48 h without GC2 or with 3 µM of GC2 and viable cells were counted. The growth rate of treated samples was expressed as % of the control sample growth treated with 3 µM of GC2.

FIGS. 5 (A)-(B) presents images illustrating alterations in cell compartments and cytoskeleton induced by GC2 treatment in melanoma cells. (A) Acidic vesicles detected by vital staining with Lysotracker® Red in SKMel28 cells: untreated (a), 3 h (b) and 8 h (c) after incubation with 6 µM GC2. (B) SKMel28 (a, b, c, d, e, f, g, h) and MelJuSo (i, j, k, l, m, n, o) nontreated cells (−GC2) and cells treated with 6 µM GC2 for 3 h (+GC2) or with cytochalasin D for 30 min (o) were analyzed with molecular markers for early endosomes (a, e, i, l), lysosomes (b, f, j, m), actin (c, g, k, n, o) and tubulin (d, h) by (immuno)fluorescence microscopy.

FIGS. 6 (A)-(C) presents results of monitoring autophagy and apoptosis in GC2 treated melanoma cells. (A) MelJuSo (a, b, e, f), B16F10 (c, g) and MNT-1 (d, h) cells were treated with 6 µM GC2 (+) for 4 h (a, c, d), 24 h (b), 48 h (e) and the morphology of vacuolar compartments (indicated by arrows) was observed by contrast phase microscopy and compared with untreated controls (−). (B) MelJuSo cells transiently transfected with an autophagic marker, GFP-LC3, and further cultured without GC2 (a or e) or treated with 6 µM of GC2 (b, c or f, g) were analyzed with cells containing GFP only and treated with 6 µM GC2 (d or h) by fluorescence (a, b, c, d) and contrast phase microscopy (e, f, g, h). (C) B16F10 cells cultured in normal conditions (a) or treated with 6 µM of GC2 for 5 h (b, c), 8 h (d) and 24 h (e, f) were labeled with the apoptotic marker Alexa Fluor® 488-annexin V and with PI and analyzed by contrast phase (b) or fluorescence (a, c, d, e, f) microscopy. Cells that did not contain vacuoles (b) were positive for annexin V (c) and were indicated as +.

FIGS. 7 (A)-(B) presents results of analysis for two metastatic cell lines treated with GC2 using annexin V/PI double labeling. (A) Cells were treated for indicated time periods with 6 µM of GC2 (labeled as +GC2) or untreated controls (labeled as −GC2) were simultaneously labeled with Alexa Fluor® 488-Annexin V and PI and analyzed by flow cytometry for vital (Low Left), apoptotic (Low Right), necrotic (Upper Right) cells. (B) Quantification of cell populations in B16F10 or MNT-1 control (−) and treated cells (+) from (A) was done by using CellQuest® software.

FIG. 8 demonstrates an expression of MMP-2 secreted by glioblastoma multiform cells treated with GC2. Culture medium, in which untreated T11 cells (0 µM) or treated with different concentrations of GC2 (0.65 µM, 1.25 µM, 2.5 µM and 5 µM), were grown for 20 h, was concentrated and analyzed for the presence of MMP-2 by Sodium Dodecyl Sulphate PolyAcrylamide Gel Electrophoresis (SDS-PAGE) gelatin zymography. MMP-2 is vizualised as a clear band of approximately 70 kDa.

DETAILED DESCRIPTION

Unless otherwise specified "a" or "an" means one or more.
DTIC stands for 5-(3,3-dimethyl-1-triazeno)-imidazole-4-carboxamide, which is also known as dacarbazine and Daltrizen®.
GC2 is (2S,3R,4R,5S)-3,4-dihydroxy-N-nonyl-5-octyl-2 hydroxymethylpyrrolidinium acetate.
GFP stands for a green fluorescent protein.
IC50 is a drug concentration achieving 50% reduction of cell viability.
MMP stands for a matrix metalloproteinase enzyme.
NB-DNJ stands for N-butyl deoxynojirimycin.
PI stands for propidium iodide.
TZM stands for temozolomide.

Introduction

Iminosugars are polyhydroxylated nitrogen heterocycles (also named azasugars). They are sugar analogues, in which the ring oxygen has been replaced by a nitrogen atom. The biological activity of iminosugars as modulators of glycoprotein processing is well established, see e.g. A. Stutz, Iminosugars as glycosidase inhibitors, Ed. Wiley-VCH, Weinheim, 1999. In particular, one member of iminosugar family, N-butyldeoxynojirimicyn (NB-DNJ) has been extensively used as a research reagent, to elucidate folding and degradation mechanisms and the role of glycan moieties in melanosomal glycoproteins from the tyrosinase family in melanoma cells, see e.g. Branza, N. B., et al. J. Biol. Chem. 275, 8169-8175, 2000; Negroiu, G., et al. J. Biol. Chem., 275, 32200-32207, 2000; Negroiu, G., et al. Biochem. J. 344, 659-665, 1999; Negroiu, G., J. Biol. Chem. 278, 27035-27042, 2003; Petrescu, S. M., et al, Biochemistry, 39, 5229-5237, 2000. Iminosugars have been proven to work as efficient drugs in the treatment of glycolipid storage disorders, see e.g. Butters, T. D., et al., Glycobiology, 15, 43R-52R, 2005, and numerous iminosugar derivatives are currently being tested for antiviral, anti-infective and anti-diabetic properties.

Disclosure

The present inventors have discovered that a proliferation of cells can be reduced by contacting the cells with an iminosugar having formula I or a pharmaceutically acceptable salt thereof:

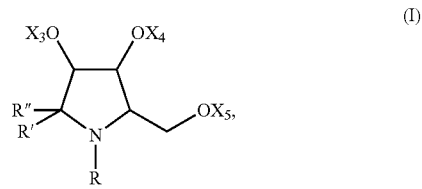

(I)

wherein R is an alkyl group comprising from 1 to 20 carbon atoms, R' is an alkyl group comprising from 1 to 20 carbon atoms, R" is hydrogen or an alkyl group comprising from 1 to 20 carbon atoms; and $X_3$, $X_4$ and $X_5$ are each independently selected from the group consisting of hydrogen, benzyl, t-butyldimethylsiloxy radical and triphenylmethyl.

The present inventors have also discovered that an iminosugar having formula I or a pharmaceutically acceptable salt thereof can reduce a secretion of a matrix metalloproteinase enzyme in mammalian cells.

Iminosugars

Iminosugars having formula I and methods of their synthesis are disclosed in U.S. patent application Ser. No. 11/514,339 to Moriarty R. M., et al. filed Sep. 1, 2006 and in Moriarty, R. M., et al., Org. Lett., 2006, 8(16): 3465-3467, which are both incorporated herein in their entirety.

In some embodiments, the iminosugar can have formula II

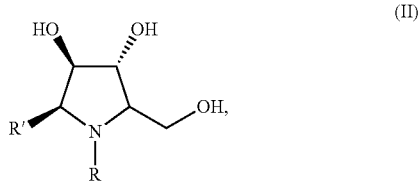

where R and R' are each alkyl groups.

Alkyl groups include straight chain and branched alkyl groups and cycloalkyl groups. Alkyl groups can have from 1 to about 20 carbon atoms. Examples of straight chain alkyl groups include, but not limited to, methyl, ethyl, n-propyl, n-butyl, n-pentyl, n-hexyl, n-heptyl, n-octyl, n-nonyl, n-decyl, n-undecyl and n-dodecyl groups. Examples of branched alkyl groups include, but are not limited to, isopropyl, iso-butyl, sec-butyl, tert-butyl, isopentyl, and 2,2-dimethylpropyl groups. Cycloalkyl groups are cyclic alkyl groups such as, but not limited to, cyclopropyl, cyclobutyl, cyclopentyl, cyclohexyl, cycloheptyl, and cyclooctyl groups.

Alkyl groups may be substituted or unsubstituted. Representative substituted alkyl groups may be substituted one or more times with any of the groups listed above, for example, amino, oxo, hydroxy, cyano, carboxy, nitro, thio, alkoxy, and F, Cl, Br, I groups.

In some embodiments, R group can be an alkyl group having from 6 to 13 carbon atoms. Preferably, R group is a straight alkyl group having from 6 to 13 carbon atoms, such as n-$C_6H_{13}$, n-$C_7H_{15}$, n-$C_8H_{17}$, n-$C_9H_{19}$, n-$C_{10}H_{21}$, n-$C_{11}H_{23}$, n-$C_{12}H_{25}$ and n-$C_{13}H_{27}$. In some embodiments, R' can be an alkyl group having from 5 to 12 carbon atoms. Preferably, R' group is a straight alkyl group having from 5 to 12 carbon atoms, such as n-$C_5H_{11}$, n-$C_6H_{13}$, n-$C_7H_{15}$, n-$C_8H_{17}$, n-$C_9H_{19}$, n-$C_{10}H_{21}$, n-$C_{11}H_{23}$ and n-$C_{12}H_{25}$.

A compound of formula I can be in the form of a salt derived from an inorganic or organic acid. Examples of such a salt include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate, undecanoate, and mixtures of any two or more thereof.

Cells

Cells that can be affected by a contact with a compound of formula I can be any type of cells. In some embodiments, the cells can be plant or animal cells. In some embodiments, the cells can be mammalian cells. The mammalian cells include, but not limited to, murine cells, canine cells and human cells.

Cells to be contacted with a compound of formula I can be cells affected by a physiological condition or a disease that leads to an abnormal or uncontrolled proliferation of the cells. Such condition can be, for example, cancer or tumor.

Cells with uncontrolled proliferation in the absence of a compound of formula I can be tumor cells. In some embodiments, the tumor cells can be melanoma cells, such as primary tumor melanoma cells and metastatic melanoma cells. Various tumor cells are available through public depositories, such as American Type Culture Depository (ATCC) or German Collection of Microorganisms and Cell Cultures (DSMZ).

Contacting with a compound of formula I can reduce a proliferation rate of contacted cells compared to a proliferation rate of non-contacted cells by at least 1.4 times or at least by 1.8 times.

Contacting with a compound of formula I can interfere with a cell cycle of the cells by, for example, increasing a proportion of cells in G0 and/or G1 phases and decreasing a proportion of cells in G2 phase.

Contacting with a compound of formula I can also result in cells' death via autophagy and/or apoptosis.

Tumors

Due to their ability to reduce proliferation of cells, compounds of formula I can be used for treatment of physiological conditions or diseases associated with uncontrolled cell proliferation, such as tumor or cancer. For example, a compound of formula can be administered to a subject affected by a physiological condition or disease associated with uncontrolled cell proliferation. The compound of formula I can be administered in doses at least 50 times lower or at least 100 times lower or at least 200 times lower or at least 500 times lower than a dose of DTIC used for treatment of the same condition or disease.

MMP Mediated Diseases

Due to their ability to reduce a secretion of matrix metalloproteinase enzyme, compounds of formula I can be used for treatment of physiological conditions and diseases associated with an elevated MMP level. Such conditions and diseases include atherosclerotic plaque rupture, aortic aneurism, heart failure, restinosis, periodontal disease, corneal, ulceration, cancer metastasis, tumor angionesis, arthritis or other autoimmune or inflammatory disorders.

In particular, compounds of formula I can used for treatment of tumors associated with an elevated MMP level. Tumors associated with elevated levels of MMPs include, but not limited to, malignant melanoma, see e.g. Nikkola J. et al., International Journal of Cancer, vol. 97, no. 4, pp. 432-438, 2002, and Nikkola J., et al., Clin Cancer Res. 2005 Jul. 15; 11(14):5158-66; ovarian carcinoma, see e.g. B. Davidson, et al., Clinical and Experimental Metastasis, 17, (10), 799-808, 1999 Lewandowski K. C., et al. J. Clin. Endocrinol. Metab. 2006 March; 91(3):1173-7; lung cancer, see e.g. Koc M., et al., Tumori. 2006 March-April; 92(2):149-54; brain tumors, see e.g. Sarkar S., et al. Cancer Res. 2006 Dec. 15; 66(24):11771-80, Jasti S. et al. Cancer Research 53, 2208-2211, May 15, 1993; cervical cancer, see e.g. Christine Gilles, et al., International Journal of Cancer, 65, (2), 209-213, 1995. In particular, the compounds of formula I can be useful for treatment of astrocytic tumors, such as pilocytic astrocytoma, fibrillary astrocytoma, anaplastic astrocytoma and glioblastoma multiformis. Due to their ability to reduce a secretion of matrix metalloproteinase enzyme, compounds of formula I can prevent and/or control tumor invasion and metastasis.

Administration

A compound of Formula I or a pharmaceutically acceptable salt thereof can be administered to a subject in need thereof, such as a mammal and in particular a human, orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral, as used herein, includes subcutaneous, intravenous, intramuscular, or intrasternal injection, or infusion techniques.

In some embodiments, injectable preparations comprising a compound of Formula I or a pharmaceutically acceptable salt thereof are provided. For example, injectable aqueous or oleaginous suspensions, may be formulated according to the known art using suitable dispersing or wetting agents and suspending agents. In some such embodiments, the injectable preparation is a sterile injectable solution or suspension in a pharmaceutically acceptable diluent, solvent, vehicle, or medium, such as, but not limited to alcohols such as 1,3-butanediol, water, Ringer's solution, isotonic sodium chloride solution, fixed oils such as mono- or diglycerides, fatty acids such as oleic acid, dimethyl acetamide, surfactants including ionic and non-ionic detergents, and polyethylene glycols, or a mixture of any two or more thereof.

Suppositories for rectal administration of the compounds discussed herein may be prepared by mixing the active agent, or agents, with a suitable excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

In some embodiments, dosage forms for oral administration include capsules, tablets, pills, powders, and granules. In such dosage forms, the compound of formula I or the pharmaceutically acceptable salt thereof may be combined with one or more adjuvants appropriate to the indicated route of administration. In some such embodiments, the compound of formula I or the pharmaceutically acceptable salt thereof, are mixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, polyvinyl alcohol, or a mixture of any two or more thereof. In some embodiments, the dosage form includes a controlled-release formulation as can be provided, for example, in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

In other embodiments, formulations for parenteral administration are in the form of aqueous or non-aqueous isotonic sterile injection solutions or suspensions. In such embodiments, solutions and suspensions are prepared from sterile powders or granules having one or more of the carriers or diluents mentioned for use in the formulations for oral administration. The compound of formula I or the pharmaceutically acceptable salt thereof may be dissolved in water, polyethylene glycol (PEG), propylene glycol, ethanol, corn oil, cottonseed oil, peanut oil, sesame oil, benzyl alcohol, sodium chloride, various buffers, or a mixture of any two or more thereof. Other adjuvants and modes of administration are well and widely known in the pharmaceutical art.

In other embodiments, liquid dosage forms for oral administration are provided. Such liquid dosage forms may include, but are not limited to, pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The invention is further illustrated by, though in no way limited to, the following examples.

Example

Materials and Methods

Reagents, Antibodies.

Reagents used for synthesis of GC2 were as follows: 2,3,5-tri-O-benzylD-arabinofuranose, nonyl, amine 98%, 2.0 M octylmagnesium bromide in diethylether and trifluormethansulfonic anhydride all purchased from Aldrich Solvents; dichlormethane, pyridine, and tetrahydrofuran all delivered anhydrous in Sure/Seal™ bottles from Aldrich.

A stock solution of 5 mM GC2 in GC2 buffer was prepared and stored at −20° C.

GC2 Buffer:

solution A: chloroform:methanol:water 10:10:3; Solution B: 150 mM NaCl in phosphate buffered saline (PBS) and 0.5% Tween® 20; mix: 1 part of solution A with 50 parts of solution B.

Daltrizen®, also known as dacarbazine and DTIC, was from S. C. Sindan-Pharma S.R.L. Romania. A 10 mg/ml stock solution of DTIC was prepared in PBS.

Both GC2 and DTIC solutions were sterile filtered before being added to cells. Propidium iodide (PI), Trypan blue 0.4% solution, cytochalasin D, RNaze and Hoechst 33342 were from Sigma.

Lysotracker® Red, Alexa Fluor® 594 goat anti Human, Alexa Fluor® 594 goat anti Mouse, Alexa Fluor® 488 annexin V, mouse anti-α tubulin, Alexa Fluor® 594 phalloidin were from Invitrogen Molecular Probes.

CellTiter 96® AQ$_{ueous}$ One solution Cell Proliferation Assay was from Promega Corporation, Madison, Wis.; human-CD107A was from Fitzgerald Industries International, USA; mouse anti-EEA1 was from BD Transduction Laboratories. EGFP-LC3 was subcloned in pEGFP-C2 vector from Clontech Laboratories, Inc., resulting in a plasmid encoding the fusion protein EGFP-LC3.

Cell Lines.

Mel Juso is a human melanoma established from a primary tumor of a 58-year-old woman with melanoma, see e.g. Ziegler-Heitbrock et al., Cancer Res. 45: 1344-1350, 1985. Mel Juso cells are available at German Collection of Microorganisms and Cell Cultures (DSMZ, Braunschweig, Germany) under accession number ACC72.

SKMel 28 is an amelanotic metastatic melanoma. SKMel 28 cells are available from American Type Culture Collection (ATCC) under accession number HTB-72.

MNT-1 is a highly pigmented metastatic melanoma cell line.

B16F10 is a murine metastatic melanoma available from ATCC under accession number CRL-6475. B16F10 is an established model for metastasis, see e.g. Jean A. Engbring, et al. Cancer Res. 62, 3549-3554, 2002.

T11 is an established glioma cell line from a patient with glioblastoma multiformis.

Cells were cultured in RPMI 1640 medium (all melanoma cell lines) or DMEM medium (T11 glioma cells) containing 10% (volume to volume, v/v) Fecal Calf Serum (FCS)

(Sigma), 50 U/ml penicillin and 50 mg/ml streptomycin (Life Technologies). The cells were grown in an atmosphere of air/$CO_2$ (19:1) at 37° C.

Cell Treatments.

Cells were cultured at indicated densities for 24 h, medium was removed and the incubation was continued in a fresh culture medium containing various GC2 or DTIC concentrations. In control experiments, cells were grown in a culture medium containing GC2 buffer.

Cell Viability Assay.

The standard methanethiosulfonate (MTS)-3-(4,5-dimethylthiazol-2-yl)-5-(3-carboxymethoxyphenyl)-2-(4-sulphophenyl)-2H-tetrazolium inner salt solution assay was performed in order to examine the cytotoxic/cytostatic effect of GC2 on melanoma cells. Briefly, $7.5 \times 10^3$ cells were seeded in 96-well microtiter plates (Nunc). After an overnight incubation, serial dilutions of GC2 or DTIC were added in triplicate to a final volume of 100 µl. The blank was represented by a culture medium without cells containing the highest GC2 or DTIC concentration. After 24 h of incubation 20 µl MTS was added to each well and all samples were incubated for 3 h at 37° C. An absorbance of each well was read at 450 nm in a microplate reader. A percentage of cell viability was calculated considering that 100% cell viability was represented by an absorbance of untreated samples (blank absorbance). Alternatively, the number of viable cells was determined by Trypan blue exclusion test. Melanoma cells treated with GC2 were trypsinized and cells negative for blue staining (viable cells) were counted using a hemocytometer.

Cell Cycle Distribution Analysis.

Cell cycle analysis in melanoma cells treated with GC2 was performed by determining DNA content using propidium iodide (PI) staining. PI intercalates into the major groove of double stranded DNA and produces a highly fluorescent adduct that can be excited at 488 nm and with a broad emission centered at 600 nm, see e.g. Krishan A. J. Cell. Biol. 66, 188, 1975. Melanoma cells ($20 \times 10^4$) were cultured in 25 $cm^2$ tissue culture flasks for 24 h, followed by a further incubation for indicated time periods with 6 µM GC2. After treatment, adherent cells were trypsinized and a number of viable cells was determined by trypan blue exclusion. 20×04 cells were re-suspended in 200 µl FACS buffer (2% FCS in PBS) and fixed with 600 µl absolute methanol, dropwise added under gentle vortexing, for at least 2 h at −20° C. Fixed cells were washed with FACS buffer, centrifuged for 5 min at 1500 rpm, at 4° C., and incubated for 30 min, in the dark, at room temperature (RT) with 200 µl PI staining solution in 3.8 mM sodium citrate (10 µl RNaze 10 µg/ml previously boiled for 5 min and 1 µl PI 10 mg/ml). The staining solution was removed by centrifugation and the cell pellet was re-suspended in 200 µl FACS buffer. Samples were analyzed for DNA content using a FACScan™ using CellQuest™ software (Becton Dickinson, San Jose, Calif.).

Immunofluorescence.

Tumor cells were cultured 24 h on cover glasses, treated with GC2, and processed as described in Negroiu, G., et al. J. Biol. Chem. 278, 27035-27042, 2003. The acidic vesicular compartments were detected following incubation of live cells GC2 treated with Lysotracker® Red (0.125 µl/ml culture medium) for 30 min at 37° C. Fixed cells were incubated with the following primary antibodies: mouse anti-EEA1 (1:100), human-CD107A (anti-Lamp1) (1:50), a mouse anti-α tubulin (1:200) followed by an appropriate Alexa Fluor® 488 conjugated secondary antibodies (1:400) or with Alexa Fluor® 594 phalloidin. Finally, nuclei of fixed cells were stained with 5 mM Hoechst dye 33342. Cells were washed three times with PBS and mounted in Vectashield® mounting medium. Live or fixed cells were observed with a Nikon Eclipse E 600 fluorescent microscope and images were processed using Adobe® Photoshop® 5.0 software.

Autophagic Vesicle Detection.

LC3 is a protein recruited to an autophagosome membrane. The recruitment process is essential for autophagy and LC3 is a specific marker of the process, see Kabeya Y., et al., EMBO J. 19, 5720-5728, 2000. To demonstrate an induction of autophagy, a GFP-tagged LC3 expression vector was used. Cells were transiently transfected with GFP-LC3 plasmid DNA using the liposomal transfection kit Lipofectamine PLUS™ Reagent (Gibco-BRL) as described in Negroiu, G., et al., J. Biol. Chem. 278, 27035-27042, 2003. 24 h after transfection cells were treated with GC2 for the indicated time periods and analyzed by fluorescence microscopy.

Apoptosis Detection Assay.

Apoptosis in GC2-treated melanoma cells was detected using Annexin V and PI double labeling assay, see van Engeland, M., et al., Cytometry, 31, 1-9, 1998. Annexin V/PI labeling was applied to both fluorescence microscopy and flow cytometry following the protocol supplied by the manufacturer. Briefly, for fluorescence microscopy analysis adherent cells (approximately $16 \times 10^4$) treated with GC2 were washed with annexin V binding buffer, and incubated with Alexa Fluor® 488 Annexin V (5 µl in 1 ml annexin V binding buffer) for 15 min at RT, in the dark, to which 0.2 µg PI was added. Live cells were washed with annexin V binding buffer and examined by microscopy. For flow cytometric analysis, cells treated with GC2 were harvested by trypsinisation and a number of viable cells was counted. $16 \times 10^4$ cells were re-suspended in 0.2 ml annexin V binding buffer and treated in the same were adherent cells. Finally, labeled cells were analyzed with a FACScan™ using CellQuest™ software (Becton Dickinson, San Jose, Calif.).

MMP Analysis by Gelatin Zymography.

T11 cells were grown in a complete DMEM medium until they reached 80% confluency. The cells were washed using DMEM medium without serum and incubated for 20 h with various concentrations of GC2 shown in preliminary experiments not to affect cell viability. The culture medium was collected, centrifuged at 2000 rpm, for 5 min, to remove the cells in suspension. The culture medium was further concentrated five times by ultrafiltration on centricon membranes (molecular weight cut off 30,000 from Milipore). Three parts of medium containing equal amounts of protein (20 µg) were mixed with one part of Laemmnli buffer without reducing agent. Samples were applied on a gel of 8% polyacrylamide impregnated with 0.5 mg/ml denaturated type I collagen (gelatin) and separated electrophoretically. The gel was washed twice with 50 mM Tris-HCl, 5 mM $CaCl_2$, 1 mM $ZnCl_2$ containing 2.5% Triton® X-100, 30 min each, and further incubated in the same buffer without Triton® X-100, overnight at 37° C. The gel was stained with 0.1% Coomassie™ Brilliant Blue R-250 and destained with methanol: acetic acid:water solution, 3:1:6. MMP activity was visualized as clear bands on the blue gel background.

Results

GC2 Synthesis.

FIG. 1A shows a compound of formula II. Compound GC2 is an acetate of the compound of formula II with R' being n-$C_8H_{17}$ and R being n-$C_9H_{19}$. In order to synthesize the compound of formula II, such as the compound GC2, a reaction scheme presented in FIG. 1B can be used. For synthesis of the GC2 compound, 2,3,5-tri-O-Benzyl-D-arabinofuranose (a), which is commercially available, was reacted in dichloromethane with n-nonylamine in excess to afford a compound (b), which was used without further purification in the next step. Reaction with octyl magnesium bromide in dry THF under nitrogen, afforded an amino-alcohol (c), which was purified by chromatography. The purified compound (c) was reacted with trifluoromethanesulphonic anhydride in dry pyridine under a nitrogen atmosphere when cyclization occurred affording a compound (d). Catalytic hydrogenation removed the protecting benzyl groups and afforded a compound (e), which is the GC2 compound.

The Effect of GC2 on the Viability of Different Melanoma Cell Lines.

Five melanoma cell lines available (MelJuSo, MNT-1, SKMel28, B16D2 and B16F10) were treated for 24 h with concentrations of GC2 ranging from 0 µM to 18 µM, in order to determine whether GC2 has a cytostatic/cytotoxic effect on these tumor cells. Cell viability was determined by MTS assay and a drug concentration resulting in reducing a number of viable cells by 50% represented IC50. The results presented in FIG. 2A, show that a viability of all studied melanoma cells was affected by GC2 in a dose dependent manner. For four cell lines (MelJuSo, MNT-1, SKMel28 and B16F10) the IC50 was between 7 µM and 8 µM, and, for B16D2, 11 µM.

The same five cell lines were exposed to DTIC, which may be considered the most active agent for treating malignant melanoma and is approved by the FDA (FIG. 2B). The IC50 for DTIC was in the range between 3 mM and 4 mM, in agreement with data reported by others using DTIC on different melanoma cell lines, see Lev, D., et al., J. Clin. Oncol. 22, 2092-2100, 2004.

Comparison of the data for GC2 and DTIC demonstrates that the same effect on amelanoma cell viability was achieved using a concentration of a maximum 11 µM of GC2 versus 4 mM of DTIC, when both drugs were tested under the identical conditions.

Based on the above results, the subsequent experiments investigating a mechanism of GC2 action on melanoma cells used a concentration of 6.0 µM GC2.

GC2 Treatment Interferes with Cell Cycle Phases in Melanoma Cells.

To examine if GC2 affects a cell cycle in melanoma cells a flow-cytometric analysis of DNA in MelJuSo and B16F10 cells treated with GC2. The data in FIG. 3 show that following a 24 h treatment with GC2, the positions of peaks in treated cells and untreated controls remained unchanged in terms of PI values. However, the peak areas representing a proportion of surviving cells in G0/G1 phase increased from 51.20% to 60.00% in MelJuSo cells and from 45.42 to 53.74% in B16F10 cells, whereas a number of cells in G2 phase decreased from 17.7% to 8.48% in MelJuSo cells and from 21.68% to 16.96% in B16F10 cells. These results demonstrate that in both primary and metastatic cell lines GC2 induced cell cycle arrest in G1 phase.

GC2 Acts as a Cell-Cycle Specific Drug.

In order to be successful, chemotherapy schedule can be set based on a type of targeted cells, a rate, at which the cells divide, and a time, at which a given drug is likely to be effective. Melanoma cells have versatile mechanisms to survive treatments with most chemotherapeutical drugs. Whether a specific scheduling of GC2 therapy is important was investigated by studying how a growth rate of melanoma cells is affected by incubation with a single dose of GC2 for a prolonged time period and with multiple GC2 doses freshly added every 24 h. Because of its high proliferation rate, a metastatic cell line B16F10 was selected for these experiments. The cells were cultured for 72 h under the following conditions: 1) in the absence of GC2 (control sample-C), 2) with a single GC2 dose of 6.0 µM (sample-S), and 3) with multiple GC2 doses of 6.0 µM freshly added every 24 h (sample-S). A number of viable cells was determined by Trypan blue exclusion test and a growth rate was calculated in order to estimate an anti-proliferative effect of GC2. Under normal drug-free conditions, B16F10 cells approximately double their number every 24 h (FIG. 4A). Incubation with a single dose of GC2 decreased the growth rate from 2.29 to 1.26 for 24 h incubation and from 7.26 to 3.7 for 72 h incubation. Still, the growth rate for sample S at 24 h and 72 h was 1.26 and 3.7, respectively, indicating that the cells are still able to proliferate during an extended incubation with a single drug dose. Cells treated with GC2 freshly added every 24 h had the lowest growth rate of 2.02.

DNA analysis of the surviving cells after 72 h incubation with GC2 was performed by flow cytometry (FIG. 3B). A histogram profile of untreated control cells at 72 h shows clearly separated peaks representing cell populations in G1, S and G2 phase. In samples S and S the positions of the G1, S and G2 peaks are significantly shifted to lower values of PI staining intensity, indicating that the number of cells in the sub-G1 phase increased. In addition, G1 and G2 peaks in the S and S* samples are less separated compared to the control sample C. These data demonstrate that cells exposed for 72 h to GC2 bind less PI, which indicates that such cells have altered DNA structures. Also, less cells are in the S phase in the cells exposed for 72 h to GC2 compared to the untreated control C at 72 h (FIG. 4B) or with cells treated with GC2 for 24 h (FIG. 3).

Tumor treatment strategies often involve periods of drug administration alternating in cycles with periods of drug withdrawal or drug administration but in lower doses, so that in the latter periods a patient can recover from side effects of the drug. Such treatment strategies, however, can also benefit the tumor, which can up regulate survival mechanisms and develop resistance to further drug exposure. Such situation was mimicked in vitro by analyzing a proliferation rate of progenies of GC2 treated cells, which were subsequently cultured in the absence of GC2 or at lower GC2 concentrations.

Equal numbers of B16F10 cells previously cultured for 72 h 1) without GC2 (C), 2) in the presence of a single GC2 dose of 6 µM (S) or 3) multiple GC2 doses of 6 µM freshly added every 24 h (S*) were further incubated either without GC2 (0 µM) or with a lower GC2 concentration (3 µM). At the end of a 48 h incubation period a number of viable cells was determined by Trypan blue exclusion test and a percentage of cell growth was calculated considering a cell number cultured with 3 µM of GC2 for 48 h to be 100%. Cells cultured with a single dose of GC2 for 72 h followed by 48 h without the drug proliferated at a rate of 99%. The rate decreased to 70% after the additional 48 h incubation of these cells in the presence of 3 µM GC2 (FIG. 4C). Cells previously exposed to multiple doses of freshly added drug had a lower proliferation rate (43%) despite being subsequently cultured without drug. The lowest growth rate, (5%) was registered for the cells previously exposed to multiple doses of freshly added drug for 72 h and then further grown for 48 h in the presence of 3 µM GC2.

These data demonstrate that both primary and metastatic melanoma cells, that survive after a prolonged GC2 treatment (72 h), have DNA structure altered by the treatment and are temporarily arrested in G1 phase because of the treatment. Progenies of cells extensively exposed to a single GC2 dose and further cultured in normal conditions are able to proliferate at a similar rate but not higher rate than untreated parental cells. However, the antiproliferative effect of GC2 is significantly enhanced in cells exposed to multiple GC2 doses freshly added every 24 h. Such cells maintain a low proliferation rate both without subsequent drug exposure and after subsequent exposure to a lower drug concentration. The highest antiproliferative effect of GC2 was achieved when a fresh GC2 dose was added in correlation with tumor cell time period of multiplication. This indicates that GC2 acts as a cell-cycle specific drug.

GC2 Treatment Involves Formation of Acidic Vesicular Organelles and Induces Alterations of Intracellular Compartments and the Cytoskeleton An insight into mechanisms of GC2 antitumoral activity on melanoma cells has been gained by analyzing intracellular alterations, which may occur in GC2-treated cells.

A number of studies report that cellular and molecular processes that occur in response to radiation and chemotherapy involve the appearance and accumulation of acidic vesicular organelles (AVO), see e.g. Paglin, S., et al., J. Cancer Res. 61, 439-441, 2001, Kanzawa, T., et al., Cell Death and Differentiation 11, 448-457, 2004, Daido, S., et al., Cancer. Res. 64, 4286-4293, 2004.

Acidic compartments of untreated and GC2-treated tumor cells were differentiated using a lysosomotropic agent LysoTracker® Red (LT), a marker for tracking acidic organelles in live cells. These probes can be used to investigate the acidification of lysosomes and alteration of their function or trafficking that occur in the cell. In untreated SKMel28 cells (FIG. 5Aa) the LT probe has a moderate fluorescence as fine punctate structures distributed within the entire cell cytoplasm and occasionally at the cell periphery. After GC2 treatment, the LT probe accumulates in large, bright red fluorescent vesicles in a time dependent manner (FIG. 5Ab and c), indicating that the novel structures formed in GC2-treated cells are related to the acid vacuolar system.

Whether tumor cell compartments and cytoskeletal elements are altered by GC2 treatment was analysed utilizing molecular markers for two main cell compartments: 1) EEA1 for early endosomes, which are accessed first by all endocytosed molecules and 2) Lamp-1 for lysosomes, the major degradative compartment. Actin filaments were labeled with Alexa Fluor® 594 phalloidin and microtubules with an anti-α-tubulin antibody; all samples were analyzed by fluorescence microscopy. In untreated cells, EEA1 appeared in punctuate structures, in a central position for SKMel28 cells (FIG. 4Ba) or at the cell periphery for MelJuSo cells (FIG. 5Bi), whereas Lamp-1 was localized perinuclear, in vesicles, which are prominent and round shaped in SKMel28 cells (FIG. 5Bb) and small in MelJuSo cells (FIG. 5Bj). Following GC2 treatment both endocytic markers were redistributed in large substructures detected also by phase contrast microscopy. In SKMel28 cells, EEA1 decorated the periphery of newly formed vacuolar compartments (FIG. 5Be) and, in MelJuSo cells, the marker accumulated in areas spread within an entire cell body (FIG. 5Bl). Lamp-1 positive structures became also prominent and invaginated into the nuclear compartment in both SKMel28 (FIG. 5Bf) and MeJuSo cells (FIG. 5Bm) cells treated with GC2. In untreated SKMel28 or MelJuSo cells, the actin network includes long ordered filaments traversing the entire cell body (FIG. 5Bc and k). In GC2-treated cells, the pattern of the fluorescent actin marker was disrupted and appeared accumulated around large vesicular structures in SKM28 cells (FIG. 5Bg) or as fine granules concentrated at the cell periphery in MelJuSo cells (FIG. 5Bn), similar to the effect produced by cytochalasin, a well known agent causing actin depolymerization (FIG. 5Bo). In addition, microtubule staining was more dense around nucleus in the untreated SKMel28 cells (FIG. 5Bd), whereas in the cells treated with GC2, the stain accumulated underneath the plasma membrane (FIG. 5Bh).

These experiments demonstrate that large acidic compartments gradually appear in response to GC2 treatment in melanoma cells. The major compartments involved in endocytic and degradative processes display an altered morphology and the large vesicles positive for the lysosomal marker indicate that lysosomes may be engaged in fusion processes with other cell compartments. The filamentous actin network is severely disrupted, whereas the microtubule network was less affected, which may suggest that GC2 acts more specifically on the actin than on the microtubule network.

GC2 Induces Autophagy and Apoptosis in Melanoma Cells

Radiation and chemotherapeutic agents may induce autophagy in several cancer cells, see e.g. Paglin, S., et al., J. Cancer Res. 61, 439-441, 2001; Kanzawa, T., et al. Cancer Res. 63, 2103-2108, 2003; Yao, K., et al. J. Neurosurg. 98, 378-384, 2003.

Autophagy may be characterized by an appearance of double or multiple membrane cytoplasmic vesicles engulfing bulk cytoplasm and/or cytoplasmic organelles, such as mitochondria and endoplasmic reticulum, see e.g. Klionsky, D. J., Emr, S. D., Science 290, 1717-1721, 2000. Autophagosomes then may fuse with lysosomes, where their cargo material is degraded and recycled. Such a process may be associated with a normal cytoplasmic and organelle turnover that occurs in healthy cells. However, under severe stress conditions, such as certain drug treatments, autophagy may become more extensive resulting in eventually a death of the cell.

In the present study, numerous vacuolar structures were observed by a phase contrast microscopy for various melanoma cell lines within approximately 2-4 h incubation with 6 μM GC2 (FIG. 6Aa, c).

The process occurred to a lesser extent in GC2 treated MNT-1 cells (FIG. 6Ad) although their proliferation rate was also affected by GC2 (FIG. 2). Within 24 h the enlarged vacuoles fused with each other (FIG. 6Ab) and formed structures that occupied almost an entire cell body and included cellular material into cell lumen (FIG. 6Ae). These structures induced as a result of GC2 treatment looked similar to autophagic vacuoles described in Kanzawa, T., et al. Cell Death and Differentiation 11, 448-457, 2004, and Daido, S., et al., Cancer Res. 64, 4286-4293, 2004.

The localization of LC3 (microtubule-associated protein1 light chain 3), which is an established marker for autophagosome membranes, see e.g. Kabeya, Y., et al. EMBO J., 19, 5720-5728, 2000, was examined in cells treated with GC2. LC3 is newly synthetised and recruited to autophagosomal membranes when autophagy is activated and is detected as cup- and ring shaped structures, see e.g. Mizushima, N. et al. Int. J. Biochem. & Cell Biol. 36, 2491-2502, 2004. Fluorescence microscopy analysis of MelJuSo cells transiently transfected with GFP-LC3 demonstrates a diffuse distribution of green fluorescence in untreated cells (FIG. 6Ba). In contrast, in 6 μM GC2-treated cells, the GFP-LC3 distributed in a punctate pattern of bright fluorescence (FIG. 6Bb and c) in the proximity of the empty vacuolar compartments visible by a phase contrast microscopy (FIG. 6Bf and g). A possibility that the punctuate pattern is due to a nonspecific aggregation of GFP was ruled out by analyzing cells transfected with GFP only and treated with GC2 (FIG. 6Bh), as in this case, GFP showed a diffuse pattern within an entire cell body (FIG. 6Bd). In GC2-treated MNT-1 cells, very few vacuoles were observed by a phase contrast microscopy. The MNT-1 cell line was also the least positive for autophagic marker (data not shown).

In sum, GC2 treatment induces a formation of autophagic vesicles in a time dependent manner, and is well correlated with the presence of vacuoles detected by phase contrast microscopy.

A possibility that GC2 treatment causes apoptosis, which is the most common type of cell death induced by a treatment with antitumoral drugs, was also investigated. Annexin V, which interacts strongly and specifically with phosphatidylserine exposed at the outer plasma membrane during early phases of apoptosis, can be used to detect apoptosis by both microscopy and flow cytometry, see van Engeland, M., et. al., Cytometry, 31, 1-9, 1998. A combined annexin V/PI staining protocol was used. In this protocol, vital cells are negative for both annexin V and PI, apoptotic cells are negative for PI but positive for annexin V and necrotic cells are positive for both annexin V and PI. B16F10 cells treated with GC2 for different time periods and untreated controls were labeled with annexin V/PI and analyzed by fluorescence microscopy. In untreated B16F10 cells, a pattern of both annexin V and PI staining was negative (FIG. 6Ca). After 5 h of incubation with 6 µM GC2 (FIG. 6Cb), numerous cells became bright green fluorescent indicating annexin V binding to the plasma membrane (FIG. 6Cc). The cells remained PI negative demonstrating that they were in early apoptosis. After 8 h incubation, the cells became positive for PI while showing less intense staining for annexin V (FIG. 6Cd) indicating that the late apoptotic population was detected. After 24 h, many round shaped cells showing a diffuse staining for annexin V (FIG. 7Ce) were observed together with cells positive for PI only (FIG. 6Cf).

The data of FIGS. 6B and C demonstrate that mechanisms of both type I (apoptosis) and II (autophagy) cell death were activated in melanoma cells treated with GC2.

GC2 Treatment Activates Different Mechanisms of Cell Death In Different Metastatic Melanoma.

For further insight into mechanisms of GC2-induced cell death, two metastatic melanoma cell lines, B16F10 (positive for autophagic marker) and MNT-1 (less active in the autophagic process), were analyzed.

Cells cultured under normal conditions for 24 h were further treated for 5 h, 8 h or 24 h with 6 µM of GC2, labeled with annexin V and PI and quantitatively analyzed by flow cytometry for viable, apoptotic and necrotic populations (FIG. 7).

In the absence of GC2, 92.76% of B16F10 and 94.17% of MNT-1 cells are viable after 24 h time period. In these controls, both the apoptotic and necrotic cell number is approximately 6%, each representing the normal cell turnover. After 5 h of GC2 treatment, a number of viable, apoptotic or necrotic cells did not change significantly for B16F10 cells. The number of apoptotic B16F10 cells increased by 1.7 after 8 h (from 1.95% to 3.44%) and by 2.9 after 24 h (from 2.28% to 6.72%). The same effect was detected for a necrotic fraction, approximately doubled after 8 h (from 4.28% to 8.78%), and increased by a factor of 4.4 at 24 h (from 4.95% to 22.16%).

In MNT-1 cells, the apoptotic population already doubled (from 3.29% to 6.94%) after 5 h, and increased 3.5 times at 8 h (from 4.32% to 15.49%) and 7.6 times after 24 h (from 3.25% to 24.86%). Unlike B16F10 cells, the MNT-1 necrotic fraction was equal or slightly lower than the apoptotic fraction, increasing by a factor of 2.3 (from 4.24% to 10.07%) at 5 h, 2.9 (from 5.84% to 17.25%) at 8 h and 9.5 (from 2.07% to 19.18%) at 24 h.

Thus, in MNT-1 cells, apoptosis is triggered within 5 h of incubation with GC2, unlike B16F10 cells, in which a significant increase in the apoptotic population was only observed after 24 h of incubation. From 5 h to 24 h of incubation the number of apoptotic cells increased in both MNT-1 and B16F10 cells, but to a larger extent in MNT-1 cells compared to B16F10. The occurrence of necrotic cells was significantly accelerated between 8 h and 24 h incubation with GC2 in B16F10 cells, but not in MNT-1 cells. These results may suggest that MNT-1 cells are more susceptible to apoptosis than B16F10 cells. The differences between necrotic and apoptotic cell populations in B16F10 and MNT-1 cells during the time periods of GC2 incubation may suggest that probably different cell death mechanisms operate in these two cell lines.

GC2 Treatment Reduces Secretion of Matrix Metalloproteinase-2 in Glioblastoma Cells.

The invasive potential of many tumor cells is associated with an elevated level of matrix metalloproteinases (MMPs), see e.g. Chintala, S. K., et al. J. Biol. Cell 273, 13545-13551, 1998 and Rucklidge, G. J., et al. Biochem. Soc. Trans. 22, 63-68, 1994. Following MMP secretion, basal membranes and surrounding extracellular matrices are degraded and tumor cells are thus enabled to travel from a primary site and to invade other target organs.

To investigate if GC2 treatment interferes with secretion of MMPs a glioblastoma multiform cell line, T11 previously tested for its capacity to secrete MMP-2 was used. Cells were cultured for 20 h in the presence of different concentrations of GC2, established by preliminary experiments to be nontoxic for this cell line, and medium was concentrated and analyzed by Sodium Dodecyl Sulphate PolyAcrylamide Gel Electrophoresis (SDS-PAGE) gelatin zymography. Untreated cells are positive for MMP-2, which appears as a clear band of approximately 70 kDa (FIG. 8). The intensity of the MMP-2 band in GC2-treated cells is decreasing in a concentration dependent manner. The incubation with 5 µM of GC2 resulted in a total inhibition of MMP-2 secretion by the T11 glioblastoma multiform cell line.

Discussion

GC2 has a cytotoxic effect on both primary and metastatic cell lines (FIG. 2A). B16D2, a highly metastatic cell line transfected with an angiogeneic factor, was also susceptible to GC2 (IC50 11 µM). When injected in mice, B16D2 cells can induce the formation of large vascularized tumors and this murine animal model can be further useful for in vivo in testing of GC2 as a limiting drug for solid vascularized tumors.

Under identical experimental conditions, GC2 exerts its effect at significant lower concentrations (µM range) than dacarbazine (mM range (FIG. 2B). IC50 doses established for GC2 on melanoma cells (FIG. 2A) are similar or even lower than data reported by other in vitro studies for various antitumoral drugs: 5 µM for betulinic acid, see e.g. Sawanda, N., et al. British Journal of cancer, 90, 1672-1678, 2004; 1 mM for DTIC Lev, D.; et al., J. Clin. Oncol. 22, 2092-2100, 2004; 200 µM for temozolomide (TZM), see e.g. Kanzawa, T., et al., Cell Death and Differentiation 11, 448-457, 2004; or 100 µM for C2-ceramide Scarlatti, F., et al. J. Biol. Chem. 279, 18384-18391, 2004. GC2 has a good solubility in a solvent mixture with no toxic or other side effects to the cells, and aliphatic chains of intermediate length (C8-C9), which allow it to cross cell membranes easily.

Further studies reported have aimed at the identification of molecular targets and processes, which may interfere with GC2 antitumoral activity in melanoma cells. The dysregulation of cell cycle mechanisms represents one of the major perturbations that occur in malignant transformation, resulting in an uncontrolled proliferation of tumor cells. Numerous antitumoral drugs are alkylating agents of small molecular weight that bind directly to DNA, preventing replication or repair processes and inducing cell cycle arrest in G1 or G2 phase. However, it has been recently shown that the G1 phase of the cell cycle is characterized by a high rate of membrane phospholipid turnover and disrupting this process results in blocking the entry of G1-phase cells into S-phase, see e.g. Zhang, X. H., et al., J. Cell Sci., 119, 1005-1015, 2005. A demonstrated above, GC2 induces melanoma cell arrest in G1 phase in both primary and metastatic cells and a number of cells in S-phase decreases during an extended cell incubation with freshly added GC2 doses (FIG. 3 and FIG. 4B). Although the present invention is not limited by a theory, one can hypothesize that GC2, as a lipophilic compound with a relative high molecular weight (431 kDa) may interfere directly or indirectly with a membrane flow in tumor cells, and therefore induce G1-arrest, rather than bind directly to the DNA. In addition, the progenies of cells extensively exposed to GC2 have alterations in their DNA structure, which suggests that GC2 also interferes with mechanisms of DNA repair in the cells.

GC2 acts as a cell cycle specific drug. The progenies resulting from B16F10 parental cells treated with a single GC2 dose for 72 h are able to proliferate normally in the drug absence, whereas cells exposed to multiple GC2 doses freshly added in cycles every 24 h for 72 h (FIG. 4C) generated progenies in sub-G1 phase, with severely altered DNA, and significantly lower proliferation rate in the drug absence. This indicates that defensive mechanisms are activated in melanoma cells treated with GC2. These defensive mechanisms can be overcome by cell exposure to fresh amounts of drug, which ultimately results in limiting cell proliferation.

Treatments with different chemostatic agents induce the appearance of acidic vesicular organelles (AVO) in tumor cells and the activation of autophagy. AVO formation, see e.g. Altan, N., et al., J. Exp. Med. 187, 1583-1598, 1998, and autophagic processes, see e.g. Cuevo, A. M. Trends in Cell Biology, 4, 70-77, 2004, may serve as protective mechanisms of tumor cells to overcome a temporary exposure to drug and to allow surviving colonies to further proliferate. However, a continuous formation of AVO, see e.g. Paglin, S., et al., J. Cancer Res. 61, 439-441, 2001, and Kanzawa, T., et al., Cell Death and Differentiation 11, 448-457, 2004, or extended autophagy, see e.g. Gozuacik, D., Kimchi, A. Oncogene, 23, 2891-2906, 2004, after high level of damage may offset their protective effect leading to necrosis and death. As shown above, tumor cell response to GC2 treatment induces formation of acidic compartments (FIG. 5A). Large vacuoles including parts of bulk cytoplasm undergoing fusion processes and finally occupying the entire cell body were clearly visible by phase contrast microscopy (FIG. 6A). Severe alterations of endosomal and lysosomal compartments (FIG. 5B) and accumulation of the autophagic marker LC3 in a punctate pattern indicated formation of autophagic vesicles and initiation of autophagy (FIG. 6B). An increase in lysosomal volume in association with autophagic vesicles was also reported to occur in glioma cells treated with the antitumoral agent TZM, probably as a result of the fusion process between autophagosomes and lysosomes which occur in autophagy, see e.g. Kanzawa, T., et al., Cell Death and Differentiation 11, 448-457, 2004.

In addition to autophagy, the demonstrated presence of apoptotic cells after treatment with GC2 indicates that GC2 is capable to activate the apoptotic pathways in melanoma. This is important, as the reduced efficacy of most chemotherapeutic agents in melanoma is likely to relate to a relative inability to induce apoptosis compared to other malignant cell types, see e.g. Li G., Melanoma Res. 8, 17-23, 1998. Surprisingly, MNT-1 cells, in which very few autophagic vacuoles were observed during drug treatment, were more susceptible to apoptosis than B16F10 cells, in which the necrotic population was predominant (FIG. 7). The analysis of these two metastatic cell lines treated with GC2 revealed differences related to their apoptotic and necrotic populations and the time periods within they occurred. The interpretation of this result may be that tumor cells like B16F10, that are more capable to trigger autophagy than MNT-1 cells, may delay the GC2-induced apoptotic process. AVO formation and/or autophagy were better detected in B16F10 cells than in MNT-1 and therefore one can assume these processes temporarily operate defensively in B16F10 cells. When cyclically exposed to fresh doses of drug, B16F10 cells extend the autophagic process, which becomes a self-destructive mechanism that ultimately causes cell death.

The final findings about GC2 action in melanoma cells are related to processes and mechanisms involved in tumor invasion and metastasis. Cell motility and capacity to depolymerize the basement membranes and extracellular matrices can be key elements in tumor invasion and metastasis. In the present study, it was shown that, in addition to alterations of the intracellular compartments, GC2 treatment results in the severe alteration of actin pattern in both primary and metastatic cell lines (FIG. 5B). The punctuate actin staining induced by GC2 treatment in primary melanoma cells is similar to the actin depolymerization phenotype produced by cytochalasine D, an agent well known for its capacity to inhibit actin polymerization. Surprisingly, the pattern of the microtubule network is not altered by GC2 treatment, which indicates that GC2 action is more specific to actin.

High levels of MMPs are associated with an invasive phenotype in many tumors, see e.g. Rucklidge, G. J., et al. Biochem. Soc. Trans 22, 63-68, 1994. Therefore, the compounds that influence MMP synthesis and secretion in the extracellular environment are therapeutically significant. The induction of MMP-9 requires a polymerized actin cytoskeleton in human malignant glioma cells, see e.g. Chintala, S. K., et al., J. Biol. Cell 273, 13545-13551, 1998. In the present study, it was also shown that following GC2 treatment, the amount of MMP-2 secreted by T11 glioma cells is decreasing while the concentration of GC2 increases.

In conclusion, it was demonstrated that synthetic compound GC2, a five member ring iminosugar, has antiproliferative activity when tested in vitro on melanoma cells. The cell processes and molecular targets identified to interfere with GC2 are critical for tumor survival and spreading.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A method of reducing proliferation of melanoma cells comprising contacting the melanoma cells with a compound having formula I or a pharmaceutically acceptable salt thereof:

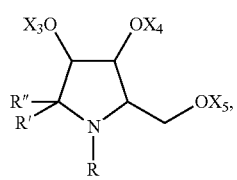

(I)

wherein R is an alkyl group comprising from 1 to 20 carbon atoms,

R' is an alkyl group comprising from 1 to 20 carbon atoms,

R" is hydrogen or an alkyl group comprising from 1 to 20 carbon atoms; and $X_3$, $X_4$ and $X_5$ are each hydrogen, wherein the contacting results in a reduced proliferation of the melanoma cells and in killing the melanoma cells.

2. The method of claim 1, wherein the compound is a compound having formula II or a pharmaceutically acceptable salt thereof:

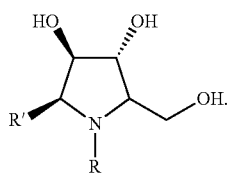

(II)

3. The method of claim 2, wherein R is an alkyl group comprising from 6 to 13 carbon atoms.

4. The method of claim 3, wherein R is n-$C_9H_{19}$.

5. The method of claim 2, wherein R' is an alkyl group comprising from 5 to 12 carbons.

6. The method of claim 5, wherein R' is n-$C_8H_{17}$.

7. The method of claim 2, wherein R is n-$C_9H_{19}$ and R' is n-$C_8H_{17}$.

8. The method of claim 1, wherein the melanoma cells are mammalian melanoma cells.

9. The method of claim 8, wherein the melanoma cells are human melanoma cells.

10. The method of claim 8, wherein the melanoma cells are murine melanoma cells.

11. The method of claim 1, wherein the melanoma cells are metastatic melanoma cells.

12. The method of claim 1, wherein the melanoma cells are primary tumor melanoma cells.

13. The method of claim 1, wherein the contacting interferes with a cell cycle of the melanoma cells.

14. The method of claim 1, wherein the contacting reduces a secretion of at least one matrix metalloproteinase enzyme in the melanoma cells.

15. The method of claim 14, wherein the contacting reduces a secretion of a matrix metalloproteinase-2 enzyme.

16. The method of claim 1, wherein the contacting results in killing the melanoma cells via at least one of an autophagy of the melanoma cells and an apoptosis of the cells.

17. The method of claim 1, wherein the contacting comprises administering an effective amount of the compound to a mammal in need thereof.

18. The method of claim 17, wherein the mammal is a human.

19. A method of reducing a secretion of a matrix metalloproteinase enzyme in cells, comprising contacting the cells with a compound having formula I or a pharmaceutically acceptable salt thereof:

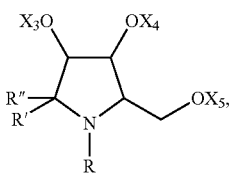

(I)

wherein R is an alkyl group comprising from 1 to 20 carbon atoms,

R' is an alkyl group comprising from 1 to 20 carbon atoms,

R" is hydrogen or an group alkyl comprising from 1 to 20 carbon atoms; and $X_3$, $X_4$ and $X_5$ are each hydrogen, wherein the contacting results in a reduced secretion of the matrix metalloproteinase enzyme in the cells.

20. The method of claim 19, wherein the compound is a compound having formula II or a pharmaceutically acceptable salt thereof:

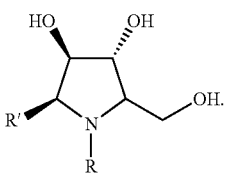

(II)

21. The method of claim 20, wherein R is an alkyl group comprising from 6 to 13 carbon atoms.

22. The method of claim 21, wherein R is n-$C_9H_{19}$.

23. The method of claim 20, wherein R' is an alkyl group comprising from 5 to 12 carbons.

24. The method of claim 23, wherein R' is n-$C_8H_{17}$.

25. The method of claim 20, wherein R is n-$C_9H_{19}$ and R' is n-$C_8H_{17}$.

26. The method of claim 19, wherein the cells are mammalian cells.

27. The method of claim 26, wherein the cells are human cells.

28. The method of claim 26, wherein the cells are murine cells.

29. The method of claim 19, wherein the cells are tumor cells.

30. The method of claim 29, wherein the cells are astrocytic tumor cells.

31. The method of claim 30, wherein the astrocytic tumor cells are glioblastoma cells.

32. The method of claim 19, wherein the contacting results in a total inhibition of the secretion of the matrix metalloproteinase enzyme.

33. The method of claim 19, wherein the matrix metalloproteinase enzyme is a matrix metalloproteinase-2 enzyme.

34. The method of claim 19, wherein the contacting comprises administering an effective amount of the compound to a mammal in need thereof.

35. The method of claim 34, wherein the mammal is a human.

\* \* \* \* \*